United States Patent
Heymes

[11] 4,288,434
[45] Sep. 8, 1981

[54] CEPHALOSPORANIC ACID DERIVATIVES

[75] Inventor: Rene'Heymes, Romainville, France

[73] Assignee: Roussel Uclaf, Paris, France

[21] Appl. No.: 886,421

[22] Filed: Mar. 14, 1978

[30] Foreign Application Priority Data

Mar. 25, 1977 [FR] France ................................ 77 08988
Dec. 5, 1977 [FR] France ................................ 77 36512

[51] Int. Cl.³ .................. A61K 31/545; C07D 501/34
[52] U.S. Cl. ..................................... 424/246; 544/28; 548/195
[58] Field of Search ........................... 544/28; 424/246

[56] References Cited

U.S. PATENT DOCUMENTS

| | | | |
|---|---|---|---|
| 3,971,778 | 7/1976 | Cook et al. | 424/246 |
| 4,007,174 | 2/1977 | Laundon | 424/246 |
| 4,098,888 | 6/1978 | Ochiai et al. | 424/246 |
| 4,103,084 | 7/1978 | Bradshaw et al. | 544/28 |
| 4,152,432 | 5/1979 | Heymes et al. | 424/246 |
| 4,166,115 | 9/1979 | Takaya et al. | 544/27 |

FOREIGN PATENT DOCUMENTS

2556736 6/1976 Fed. Rep. of Germany.

*Primary Examiner*—Paul M. Coughlan, Jr.
*Attorney, Agent, or Firm*—Hammond & Littell, Weissenberger and Muserlian

[57] ABSTRACT

Novel syn isomers of 7-amino-thiazolyl-acetamido-3-acetoxymethyl-cephalosporanic acid derivatives of the formula

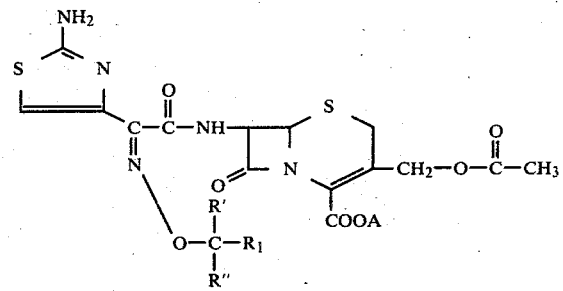

wherein $R_1$ is selected from the group consisting of —CN, —CONH$_2$ and —COOR$_1'$, $R_1'$ is selected from the group consisting of alkyl of 1 to 3 carbon atoms, hydrogen, alkali metal, alkaline earth metal, ammonium, magnesium and a non-toxic, pharmaceutically acceptable organic amine, A is selected from the group consisting of hydrogen, alkali metal, alkaline earth metal, ammonium, magnesium and a non-toxic, pharmaceutically acceptable organic amine, R' and R" are individually selected from the group consisting of hydrogen and alkyl of 1 to 3 carbon atoms with the

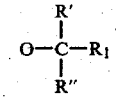

group in the syn position with the proviso that when $R_1$ is —COOR$_1'$ and $R_1'$ is hydrogen, A is hydrogen and when $R_1$ is —COOR$_1'$ and $R_1'$ is an alkali metal, alkaline earth metal, magnesium, ammonium or an organic amine, A is an alkali metal, alkaline earth metal, magnesium ammonium or an organic amine having antibiotic properties and novel intermediates and processes.

24 Claims, No Drawings

CEPHALOSPORANIC ACID DERIVATIVES

STATE OF THE ART

French Pat. No. 2,315,933 and No. 2,255,076 and Belgium Pat. No. 852,427 describe different 7-aminothiazolyl-acetamido-3-acetoxy-cephalosporanic acid derivatives.

OBJECTS OF THE INVENTION

It is an object of the invention to provide the novel compounds of formula I and to provide a novel process and novel intermediates for their preparation.

It is another object of the invention to provide novel antibiotic compositions and to a novel method of combatting infections of gram negative and gram positive bacteria in warm-blooded animals.

These and other objects and advantages of the invention will become obvious from the following detailed description.

THE INVENTION

The novel compounds of the invention are syn isomers of 7-amino-thiazolyl-acetamido-3-acetoxymethyl-cephalosporanic acid derivatives of the formula

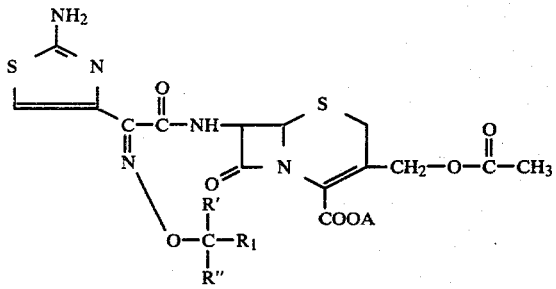

wherein $R_1$ is selected from the group consisting of —CN, —CONH$_2$ and —COOR$_1'$, $R_1'$ is selected from the group consisting of alkyl of 1 to 3 carbon atoms, hydrogen, alkali metal, alkaline earth metal, ammonium, magnesium and a non-toxic, pharmaceutically acceptable organic amine, A is selected from the group consisting of hydrogen, alkali metal, alkaline earth metal, ammonium, magnesium and a non-toxic, pharmaceutically acceptable organic amine, R' and R" are individually selected from the group consisting of hydrogen and alkyl of 1 to 3 carbon atoms with the

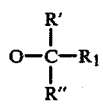

group in the syn position with the proviso that when $R_1$ is —COOR$_1'$ and $R_1'$ is hydrogen, A is hydrogen and when $R_1$ is —COOR$_1'$ and $R_1'$ is an alkali metal, alkaline earth metal, magnesium, ammonium or an organic amine, A is an alkali metal, alkaline earth metal, magnesium, ammonium or an organic amine.

Examples of lower alkyl for $R_1'$, R' and R" are methyl, ethyl, propyl and isopropyl. Examples of $R_1'$ and A are alkali metal such as sodium, potassium and lithium, alkaline earth metal such as calcium, magnesium, —NH$_4$ and non-toxic, pharmaceutically acceptable organic amines such as methylamine, diethylamine, triethylamine, trimethylamine, propylamine, N,N-dimethyl-ethanolamine, tris(hydroxymethyl) aminomethane, arginine or lysine.

Among the preferred compounds of the invention are those wherein $R_1$ is —COOR$_1'$ and $R_1'$ is alkyl of 1 to 3 carbon atoms, hydrogen, alkali metal, alkaline earth metal, magnesium, ammonium or an organic amine and R' and R" are hydrogen.

Specific preferred compounds of formula I are the syn isomers of 7-[2-(2-amino-4-thiazolyl)-2-(carbethoxymethyloxyimino)-acetamido]-3-acetoxymethyl-ceph-3-eme-4-carboxylic acid, 7-[2-(2-amino-4-thiazolyl)-2-(hydroxycarbonylmethyloxyimino)-acetamido]-3-acetoxymethyl-ceph-3-eme-4-carboxylic acid, 7-[2-(2-amino-4-thiazolyl)-2-(cyanomethyloxyimino)-acetamido]-3-acetoxymethyl-ceph-3-eme-4-carboxylic acid, 7-[2-(2-amino-4-thiazolyl)-2-(aminocarbonylmethyloxyimino)-acetamido]-3-acetoxymethyl-ceph-3-eme-4-carboxylic acid and 7-[2-(2-amino-4-thiazolyl)-2-(1-carboxy-1-methylethyloxyimino)-acetamido]-3-acetoxymethyl-ceph-3-eme-4-carboxylic acid as well as their salts with alkali metals, alkaline earth metals, magnesium, ammoniac and organic amine bases. In the latter group, particularly preferred are the syn isomers of disodium 7-[2-(2-amino-4-thiazolyl)-2-hydroxycarbonylmethyloxyimino)-acetamido]-3-acetoxymethyl-ceph-3-eme-4-carboxylate, sodium 7-[2-(2-amino-4-thiazolyl)-2-(cyanomethyloxyimino)-acetamido]-3-acetoxymethyl-ceph-3-eme-4-carboxylate, sodium 7-[2-(2-amino-4-thiazolyl)-2-(aminocarbonylmethyloxyimino)-acetamido]-3-acetoxymethyl-ceph-3-eme-4-carboxylate and disodium 7-[2-(2-amino-4-thiazolyl)-2-(1-carboxy-1-methylethyloxyimino)-acetamido]-3-acetoxymethyl-ceph-3-eme-4-carboxylate.

The compounds of the invention may exist in the form of formula I or in the form of products of the formula

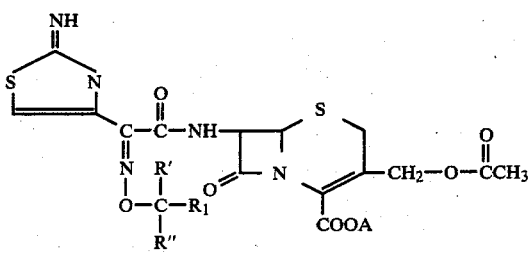

The novel process of the invention for the preparation of compounds of formula I comprises reacting a compound of the formula

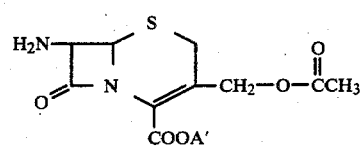

wherein A' is hydrogen or an ester group easily removable by acid hydrolysis of hydrogenolysis with an acid of the formula

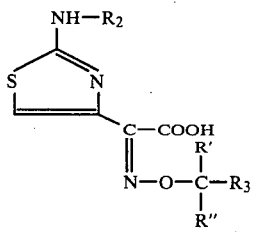

or a functional derivative thereof wherein $R_2$ is selected from the group consisting of chloroacetyl and groups easily removable by acid hydrolysis or hydrogenolysis, $R'$ and $R''$ have the above definition and $R_3$ is selected from the group consisting of —CN, —CONH$_2$ and —COOR$_1''$ and $R_1''$ is alkyl of 1 to 3 carbon atoms or an ester group easily removable by acid hydrolysis or hydrogenolysis and the group

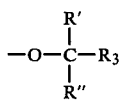

is in the syn position to obtain a compound of the formula

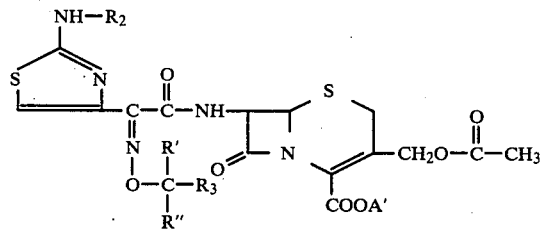

and reacting the latter with at least one member of the group consisting of thiourea, acid hydrolysis agent or hydrogenolysis to obtain a compound of the formula

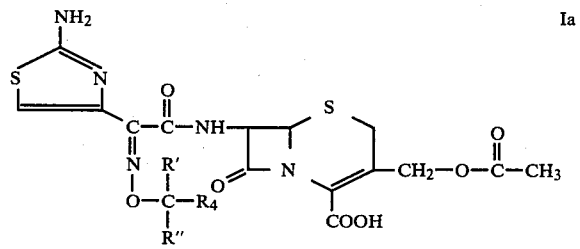

wherein $R_4$ is selected from the group consisting of —CN, —CONH$_2$ and —COOR$_2''$ and $R_2''$ is alkyl of 1 to 3 carbon atoms or hydrogen which may be salified by known methods to obtain a compound of the formula

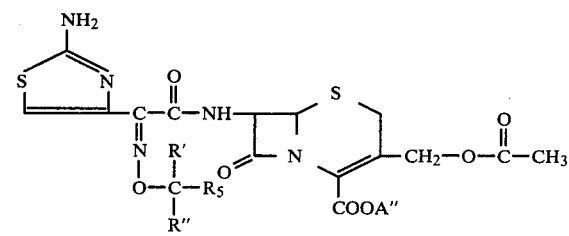

wherein $R_5$ is selected from the group consisting of —CN, —CONH$_2$ and —COOR$_3''$ and $R_3''$ is selected from the group consisting of alkyl of 1 to 3 carbon atoms, alkali metal, alkaline earth metal, magnesium, ammonium and an organic amine and $A''$ is selected from the group consisting of alkali metal, alkaline earth metal, magnesium, ammonium and an organic amine with the proviso that when $R_5$ is —COOR$_3''$ and $R_3''$ is other than alkyl of 1 to 3 carbon atoms, $A''$ is the same as $R_3''$.

Examples of groups easily removable by acid hydrolysis or hydrogenolysis for $R_2$ are tert.-butoxycarbonyl, trityl, benzyl, dibenzyl, trichloroethyl, carbobenzyloxy, formyl, trichloroethoxycarbonyl or 2-tetrahydropyranyl. Examples of esters easily removable by acid hydrolysis or hydrogenolysis for $R_1''$ or $A'$ are benzhydryl, tert.-butyl, benzyl, p-methoxybenzyl and trichloroethyl.

In a preferred mode of the said process, the 7-amino-cephalosporanic acid compound of formula II is reacted with a functional derivative of the acid of formula III such as the acid chloride or the acid anhydride such as that formed in situ with isobutyl chloroformate or dicyclohexylcarbodiimide with acid. Other acid halides or other acid anhydrides formed in situ with other alkyl chloroformates, a dialkylcarbodiimide or other dicycloalkylcarbodiimide may be used. Equally useful are other acid derivatives such as the acid azide, the acid amide or an ester of an actived acid such as formed by hydroxysuccimide, p-nitrophenol or 2,4-dinitrophenol.

The reaction of the 7-amino-cephalosporanic acid compound of formula II with isobutyl chloroformate anhydride or acid chloride of the acid of formula III is preferably effected in the presence of a basic agent such as an alkali metal carbonate or an organic tertiary amine such as N-methylmorpholine or pyridine or a trialkylamine such as triethylamine.

The transformation of the products of formula I' into the products of formula Ia is effected for replacing $R_2$ with hydrogen and replacing $R_1''$, when it is an ester group easily removable by acid hydrolysis or hydrogenolysis with $R_2''$ as hydrogen and replacing $A'$, when it is an ester group easily removable by acid hydrolysis or hydrogenolysis, with hydrogen. One or more acid hydrolysis agents are used when $R_2$ is a group easily removable by acid hydrolysis, $R_3$ is not —COOR$_1''$ in which $R_1''$ is an ester group easily removable by hydrogenolysis and $A'$ is hydrogen or an ester group easily removed by acid hydrolysis. One or more hydrogenolysis agents are used when $R_2$ is a group easily removed by hydrogenolysis, $R_3$ is not —COOR$_1''$ in which $R_1''$ is a group easily removed by acid hydrolysis and $A'$ is hydrogen or an ester group easily removed by hydrogenolysis.

The products of formula I' may be treated with one or more acid hydrolysis agents and one or more hydrogenolysis agents when at least one of $R_2$, $R_1''$ and $A'$ are a group easily removed by acid hydrolysis and at least one is a group easily removed by hydrogenolysis. The products of formula I' may be treated with thiourea followed by one or more acid hydrolysis or hydrogenolysis agents according to the groups $R_1''$ and $A'$ when $R_2$ is chloroacetyl.

The acid hydrolysis of the products of formula I' may be effected with formic acid, trifluoroacetic acid or acetic acid in the anhydrous or aqueous form. Equally useful is the zinc-acetic acid system.

When $R_2$ is tert.-butoxycarbonyl or trityl or when A' and $R_1''$ are benzhydryl, tert.-butyl or p-methoxybenzyl, the preferred acid hydrolysis agent is anhydrous trifluoroacetic acid or aqueous formic acid or aqueous acetic acid. When $R_2$, $R_1''$ and A' are trichloroethyl, the zinc-acetic acid system is preferred. When $R_1''$ and A' are benzyl and $R_2$ is dibenzyl or carbobenzyloxy, a hydrogenolysis agent such as hydrogen in the presence of a catalyst is preferred.

The reaction of a product of formula I' when $R_2$ is chloroacetyl, with thiourea is preferably effected in a neutral or acid media and the reaction is described by Masaki [JACS., Vol. 90 (1968), p. 4508].

The salification may be effected by known methods such as by reacting the free acid with a mineral base such as sodium hydroxide, potassium hydroxide or sodium bicarbonate or a salt of a substituted or non-substituted aliphatic carboxylic acid such as diethylacetic acid, ethylhexanoic acid or especially acetic acid with the preferred salts being the sodium salts. The salification may be effected with ammonium hydroxide or organic amine base such as triethylamine, trimethylamine, propylamine, N,N-dimethylethanolamine or tris (hydroxymethyl)aminomethane as well as with arginine or lysine.

For the preparation of the salts, the solvates of the free acids may also be used in place of the free acids. The solvates may be obtained with water, formic acid or an alcohol, for example. The solvates with an alcohol, preferably ethanol, may be obtained by treatment with an alcoholwater mixture of the solvate with formic acid which is then followed by concentration of the solution.

The salification is preferably effected in at least one solvent such as water, ether, methanol, ethanol or acetone and the salts may be either crystalline or amorphous depending on the reaction conditions used. The crystalline salts are preferably prepared by reacting the free acid, with a salt of the above mentioned aliphatic carboxylic acid, preferably sodium acetate. In the preparation of a sodium salt, the reaction is effected in the appropriate organic solvent such as methanol which can contain small amounts of water.

Another aspect of the invention is a process for the preparation of a compound of formula III comprising reacting in the presence of a strong base a compound of the formula

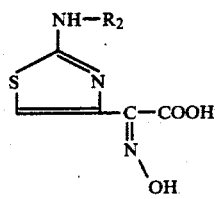  IV wherein $R_2$ is selected from the group consisting of chloroacetyl and a group easily removable by acid hydrolysis or hydrogenolysis and OH is in the syn postion with a compound of the formula

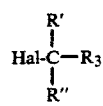  V wherein Hal is a halogen and R', R'' and $R_3$ have the above definitions to obtain the corresponding compound of formula III.

In a preferred mode of the process, the strong base is potassium tert.-butylate, sodium hydride or potassium ethanolate and the preferred halide of formula V is the bromide although the chloride or iodide are equally useful.

In a modification of the process to obtain the compounds of formula I' in the syn form, a compound of formula V is reacted in the presence of a base with a compound of the formula

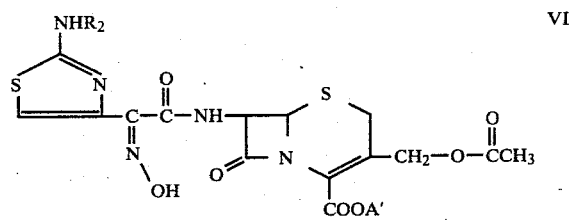  VI to obtain the corresponding of formula I'.

In a preferred mode of the latter process, the base is selected from the group consisting of triethylamine, pyridine or silver oxide and the reaction is preferably effected in a solvent selected from the group consisting of methylene chloride, benzene, acetonitrile, ethyl acetate, tetrahydrofuran, dioxane, chloroform or dimethylformamide.

A further aspect of the invention is the process for the preparation of a compound of formula VI comprising reacting isopropenyl methyl ether with a syn isomer of a compound of formula IV to obtain a compound of the formula

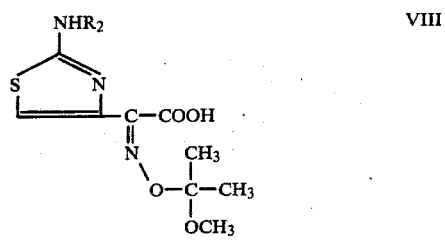  VIII reacting the said acid or a functional derivative thereof with a compound of formula II to obtain a compound of the formula

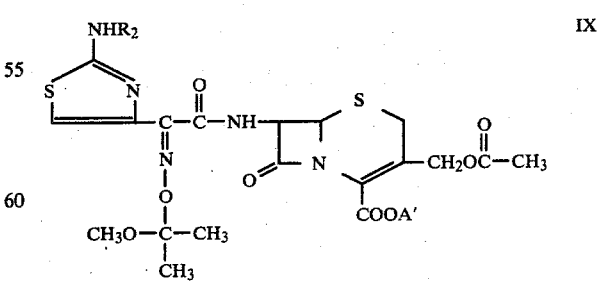  IX and when A' is hydrogen, the latter product may be esterified by known methods to obtain the compound of formula IX wherein A' is an ester group easily removed by acid hydrolysis or hydrogenolysis and the latter product may be treated under moderate acid conditions to form a compound of formula VI.

The reaction of isopropenyl methyl ether with a compound of formula IV is effected in the presence of an acid such as p-toluene sulfonic acid although the acid addition salt such as the hydrochloride of a compound of formula IV may also be used. In this case, the presence of an acid is not required and the free amine is obtained by neutralization at the end of the reaction with a base such as pyridine.

The condensation of the products of formulae VIII and II is effected in the same manner as the condensation of compounds of formulae II and III. The eventual esterification of the products of formula IX when A' is hydrogen may be effected under known conditions such as by reaction with a diazoic derivative like diazodiphenylmethane.

The transformation of the products of formula IX into products of formula VI allows cleavage of the protective group of the 1-methyl-1-methoxyethyl oxime. This reaction can be effected under acid conditions gentle enough that the $R_2$ and A' protective groups are not also cleaved under the acid conditions. A suitable example is the use of aqueous 1 N to 2 N hydrochloric acid at room temperature for a period of 30 minutes up to a few hours.

Another object of the invention is the preparation of syn isomers of compounds of the formula

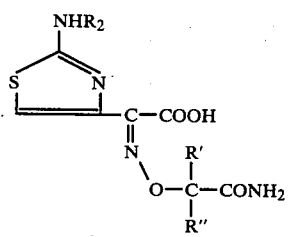

wherein R', R" and $R_2$ have the above definitions comprising reacting in the presence of a base a syn isomer of a compound of the formula

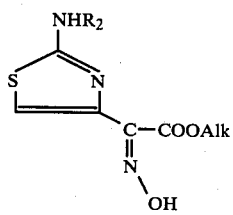

wherein Alk is alkyl of 1 to 4 carbon atoms with a compound of the formula

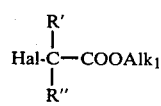

wherein $Alk_1$ is alkyl of 1 to 4 carbon atoms to obtain a compound of the formula

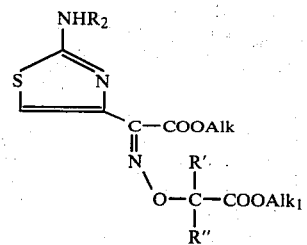

treating the latter with a base and then an acid to obtain a compound of the formula

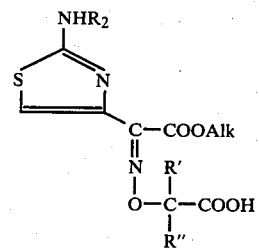

forming a reactive derivative of the said acid which is then reacted with ammonium hydroxide to form a compound of the formula

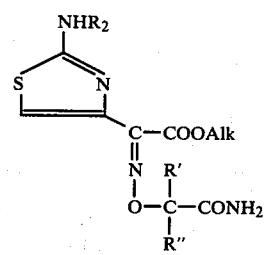

and treating the latter with a base and then an acid to obtain the corresponding compound of formula III'.

In a preferred mode of the latter process, the reaction of compounds of formula V' and X is effected in the presence of a base such as potassium carbonate although other bases such as sodium hydroxide, potassium hydroxide or triethylamine may be used as well. The halide is preferably the bromide although the iodide or chloride may be used.

The transformation of the compound of formula XI to a compound of formula XII is effected under mild conditions to avoid saponification of the —COOAlk group such as with a single equivalent of a base such as sodium hydroxide, potassium hydroxide or barium hydroxide, preferably in an ice-water bath for about one hour. The acid used thereafter is preferably aqueous hydrochloric acid although other acids such as acetic acid or dilute sulfuric acid may be used.

The reactive derivative of the compound of formula XII used is preferably a mixed anhydride formed in situ with isobutyl chloroformate but other reactive derivative may be used such as actived esters formed from hydroxysuccinimide, p-nitrophenol, o-nitrophenol or 2,4-dinitrophenol or a symetrical anhydride formed with a carbodiimide such as dicyclohexylcarbodiimide. The saponification and reacidification of the compound of formula XIII is effected under known conditions such as treatment with a base such as sodium hydroxide followed by treatment with hydrochloric acid.

Another aspect of the invention is the preparation of syn isomers of compounds of the formula

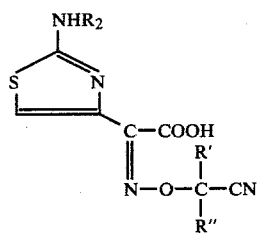

III'' comprising reacting in the presence of a base the syn isomer of a compound of formula IV with two equivalents of a compound of the formula $$\text{Hal-}\underset{R''}{\underset{|}{\overset{R'}{\overset{|}{C}}}}\text{-CN}$$

XIV to obtain a compound of the formula

XV which is then treated with a base and then an acid to obtain a compound of formula III''.

In a preferred mode of the latter process, the condensation of the products of formulae XIV and IV is effected in the presence of a base such as potassium carbonate although other bases such as sodium hydroxide, potassium hydroxide or triethylamine may be used. The saponification of the products of formula XV is effected under normal conditions followed by reacidification such as treatment with sodium hydroxide followed by treatment with hydrochloric acid.

Another modification of the process for the preparation of compounds of formula III comprises reacting a compound of formula X in the presence of a base with a compound of formula V to obtain a compound of the formula

XVI and treating the latter with a base and then an acid to form a compound of formula III.

The base present for the initial condensation is preferably potassium carbonate but other bases such as potassium hydroxide, sodium hydroxide or triethylamine may be used. The saponification of the compound of formula XVI is effected under conditions so that when $R_3$ is a group $COOR_1''$, this group is not also saponified. The treatment preferred is reaction with potassium methanolate followed by reacidification with hydrochloric acid.

It should finally be noted that for the transformation of the compounds of formula I' into compounds of formula Ia using an acid such as trifluoroacetic acid, the products of formula Ia are isolated in the form of salts between the amine of the aminothiazole ring and this acid. The free bases may be obtained by reaction of the said salt with an equivalent of a base such as pyridine.

The antibiotic compositions of the invention are comprised of an antibiotically effective amount of at least one compound of formula I and a inert pharmaceutical carrier. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, lactose, starch, magnesium stearate, cacao butter, aqueous or non-aqueous vehicles, fatty bodies of vegetables or animal origin, paraffinic derivatives, glycols, preservatives, diverse wetting agents, dispersants and emulsifiers. The compositions of the invention containing the compounds of formula I possess very good antibiotic activity against gram positive bacteria such as staphylococcus, streptococcus, particularly penicillin-resistant staphylococcus as well as against gram negative bacteria such as coliform bacteria, Klebsiella, Salmonella and Proteus.

The compositions are therefore useful in the treatment of gram positive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

The novel method of the invention for combatting bacterial infections in warm-blooded animals, including humans, comprises administering to warm-blooded animals an antibacterially effective amount of at least one compound of formula I. The compounds may be administered orally, rectally, parenterally or locally by topical application to the skin or mucous. The usual daily dose is 5 to 80 mg/kg orally in the human with the product described in examples 5, 8, 11 or 14, or 30 to 60 mg/kg intramuscularly.

The novel intermediates of the invention are the syn isomers of compounds of formula III, the syn isomers of the compounds of formula VIII wherein $R_2$ is selected from the group consisting of chloroacetyl and groups easily removed by acid hydrolysis or hydrogenolysis, the syn isomers of the compounds of formula I' and the syn isomers of the compounds of formula XVII

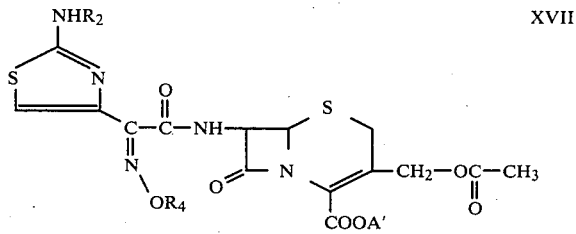

wherein A' is selected from the group consisting of hydrogen and an ester group easily removed by acid hydrolysis or hydrogenolysis and $R_4$ is selected from the group consisting of hydrogen and 1-methyl 1-methoxy-ethyl.

The compounds of formula IV and X are described in French Pat. No. 2,346,014. The products of formula V which are not known may be prepared by classical halogenation in the α-position of compounds of the formula

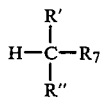

wherein $R_7$ is —CN or —COOR$_8$ and $R_8$ is hydrogen or alkyl. The products of formula V in which $R_3$ is —CONH$_2$ are prepared by amidification of the corresponding acids.

In the following examples there are described several preferred embodiments to illustrate the invention. However, it is to be understood that the invention is not intended to be limited to the specific embodiments.

EXAMPLE 1 syn isomer of 7-[2-(2-tritylamino-4-thiazolyl)-2-carbethoxymethyl-oxyimino-acetamido]-3-acetoxymethyl-ceph-3-eme-4-carboxylic acid STEP A: syn isomer of ethyl 2-(2-amino-4-thiazolyl)-2-hydroxyimino-acetate 2 g of ethyl 4-chloro-2-hydroxyimino-acetyl-acetate were added over 5 minutes to a solution of 0.8 g of thiourea in 2.4 ml of ethanol and 4.8 ml of water and the mixture was stirred at room temperature for one hour. A major part of the ethanol was evaporated under reduced pressure and the pH of the solution was adjusted to 6 with solid sodium bicarbonate. The mixture was iced and vacuum filtered and the recovered product was washed with water and dried at 40° C. under reduced pressure to obtain 1.32 g of the syn isomer of ethyl 2-(2-amino-4-thiazolyl)-2-hydroxyimino-acetate melting at 232° C.

Analysis: $C_5H_9O_3N_3S$ Calculated: %C 39.06; %H 4.21; %N 19.52; %S 14.9. Found: 38.9; 4.4; 19.7; 14.6.

STEP B: syn isomer of ethyl 2-(2-tritylamino-4-thiazolyl)-2-hydroxyimino-acetate A mixture of 43.2 g of the product of Step A in 120 ml of dry dimethylformamide was cooled to −35° C. and after the addition of 32 ml of triethylamine thereto, 60 g of trityl chloride were added in fractions thereto over 30 minutes. The temperature was allowed to rise during which a total dissolution occured and the mixture was then heated at 30° C. for an hour and was then poured into 1.2 liters of ice water containing 40 ml of 22° Bé hydrochloric acid. The mixture was stirred in an ice bath and was then vacuum filtered. The recovered product was rinsed with N hydrochloric acid and was empasted with ether to obtain 69.3 g of a hydrochloride salt which was dissolved in 5 volumes of methanol containing 120% of triethylamine. Precipitation was induced by addition of 5 volumes of water to obtain the syn isomer of ethyl 2-(2-tritylamino-4-thiazolyl)-2-hydroxyimino-acetate.

Analysis: $C_{26}H_{23}O_3N_3S \cdot \frac{1}{4}H_2O$. Calculated: %C 67.6; %H 5.1; %N 9.1; %S 6.9. Found: 67.5; 5.1; 8.8; 6.8.

STEP C. syn isomer of 2-(2-tritylamino-4-thiazolyl)-2-hydroxyimino-acetic acid

A mixture of 11.5 g of the product of Step B in 30 ml of dioxane and 25 ml of 2 N sodium hydroxide was stirred for one hour in a water bath at 50° C. and was then iced for 10 minutes and vacuum filtered. The recovered precipitate was rinsed with 50% aqueous dioxane, with a 1-1 ether-dioxane mixture and then ether and was dried to obtain 11.05 g of the syn isomer of sodium 2-(2-tritylamino-4-thiazolyl)-2-hydroxyimino-acetate. Treatment of the salt with aqueous methanol in the presence of hydrochloric acid obtained the syn isomer of 2-(2-tritylamino-4-thiazolyl)-2- hydroxyimino-acetic acid.

STEP D: syn isomer of 2-(2-tritylamino-4-thiazolyl)-2-carbethoxymethyloxyimino-acetic acid A suspension of 2.15 g of the product of Step C in 35 ml of dry tetrahydrofuran and 2.5 ml of a solution of 4 M of water in tetrahydrofuran were added over 10 minutes at 20° C. under argon to 10.5 ml of a molar solution of potassium tert.-butylate in tetrahydrofuran and the mixture was stirred at 27° C. for one hour. A solution of 1.1 ml of ethyl bromoacetate in sufficient tetrahydrofuran to obtain a volume of 10 ml was added dropwise to 5 ml of the above solution and the mixture was stirred for one hour. Another 1 ml of the molar solution of potassium tert.-butylate in tetrahydrofuran was added thereto and the mixture was stirred for one hour and was then vacuum filtered. The filter was rinsed with tetrahydrofuran and the filtrate was evaporated to dryness. The residue was taken up in a mixture of 50 ml of ethyl acetate, 15 ml of N hydrochloric acid and 15 ml of water and the mixture was stirred and decanted. The organic phase was washed with water and the wash waters were reextracted with ethyl acetate. The organic phase was dried and evaporated to dryness and the residue was added to 20 ml of ethyl acetate. Crystallization occurred and the mixture was iced and vacuum filtered. The product was rinsed with a minimum of ethyl acetate, was empasted with ether and dried to obtain 1.3 g of pure product.

The filtrate was evaporated to dryness and the residue was taken up in ethyl acetate and effloresced. The mixture was iced and was vacuum filtered and the product was rinsed with ethyl acetate and was empasted with ether to obtain a second crop of 185 mg of pure product for a total yield of 1.485 g of the syn isomer of 2-(2-tritylamino-4-thiazolyl)-2-carbethoxymethyloxyimino-acetic acid.

An analytical sample was obtained by heating to reflux a mixture of 3.14 g of the product in 30 ml of ethyl acetate during which partial dissolution occured and the mixture was cooled in ice water and was then vacuum filtered. The product was rinsed and was empasted with ether and dried to obtain 2.77 g of the said purified product.

Analysis: $C_{28}H_{25}N_3O_5S$. Calculated: %C 65.23; %H 4.89; %N 8.15; %S 6.22. Found: 65.1; 4.9; 8.0; 6.1.

RMN (CDCl$_3$-90 MHz): 6.76 ppm (proton of thiazolyl ring); 7.28 ppm (trityl group).

STEP E: syn isomer of 7-[2-(2-tritylamino-4-thiazolyl)-2-carbethoxymethyloxyimino)-acetamido]-3-acetoxymethyl-ceph-3-eme-4-carboxylic acid A solution of 345 mg of dicyclohexylcarbodiimide in 1.5 ml of methylene chloride was added under argon to a mixture of 1.55 g of the product of Step D in 22 ml of methylene chloride cooled in ice and the mixture was stirred for one hour in ice water. The mixture was vacuum filtered to remove dicyclohexylurea which was rinsed and dried. The filtrate was iced in a ice-methanol bath and a solution of 410 mg of 7-amino-cephalosporanic acid in 7.5 ml of dry methylene chloride and 0.42 ml of triethylamine was added thereto all at once. Spontaneous heating was permitted over 3 hours and then 7.5 ml of water and 3.75 ml of N hydrochloric acid were added thereto. The mixture was stirred and was vacuum filtered. The filtrate was decanted and the aqueous phase was extracted with methylene chloride. The organic phase was washed with water, dried and evaporated to dryness and the residue was taken up in 7.5 ml of ethyl acetate. The mixture was stirred one hour in ice water and was vacuum filtered. The crystals were rinsed to obtain 600 mg of product and the filtrate was evaporated to dryness to obtain 1.34 g of residue which was dissolved in 6 ml of ethyl acetate. 0.15 ml of pure diethylamine were added thereto and the mixture was progressively diluted while stirring with 35 ml of ether to obtain an insoluble gum which crystallized. The mixture was vacuum filtered and the product was rinsed with a solution of 15% ethyl acetate in ether and was empasted with ether and dried to obtain 983 g of a purified diethylamine salt. The said salt was dissolved in 10 ml of methylene chloride and 1.3 ml of N hydrochloric acid was added thereto to obtain a pH of 2. The mixture was stirred and was decanted. The organic phase was washed with water and the wash waters were reextracted with methylene chloride. The organic phase was dried and evaporated to dryness and the residue was taken up in ether and was vacuum filtered to obtain 818 mg of the syn isomer of 7-[2-(2-tritylamino-4-thiazolyl)-2-carbethoxymethoxyimino-acetamido]-3-acetoxymethyl-ceph-3-eme-4-carboxylic acid.

EXAMPLE 2 syn isomer of 7-[2-(2-amino-4-thiazolyl)-2-carbethoxymethyloxyimino-acetamido]-3-acetoxymethyl-ceph-3-eme-4carboxylic acid A suspension of 0.818 g of the product of Example 1 in 4 ml of 50% aqueous formic acid was heated at 60° C. in a water bath for 20 minutes during which triphenylcarbinol crystallized and the mixture was cooled and diluted with 4 ml of water. The mixture was stirred and was vacuum filtered and the precipitate was rinsed with water and dried to obtain 305 mg of triphenylcarbinol. The filtrate was evaporated to dryness under reduced pressure and the residue was taken up in ethanol. The mixture was evaporated to dryness and the residue was taken up in water. The solution was iced for 15 minutes and was vacuum filtered. The product was rinsed with water and dried to obtain 229 mg of the syn isomer of 7-[2-(2-amino-4-thiazolyl)-2-carbethoxymethyloxyiminoacetamido]-3-acetoxymethyl-ceph-3-eme-4-carboxylic acid.

Analysis: $C_{19}H_{21}O_9N_5S_2$. Calculated: %C 43.26; %H 4.01. Found: 43.3; 4.3.

RMN (DMSO-60 MHz): =N—O—CH$_2$—COO—CH$_2$—CH$_3$ (c)    (b)    (a)

(a) triplet centered at 1.2 ppm J = 7Hz; (b) quadruplet centered at 4.15 ppm J = 7Hz; (c) singulet at 4.66 ppm; singulet at 6.8 ppm (proton of thiazol ring).

EXAMPLE 3 syn isomer of tert.-butyl 7-[2-(2-tritylamino-4-thiazolyl)-2-tert.-butoxycarbonylmethyloxyimino-acetamido]-3-acetoxymethylceph-3-eme-4-carboxylate STEP A. syn isomer of 2-tert.-butoxycarbonylmethoxyimino-2-(2-tritylamino-4-thiazolyl)-acetic acid A mixture of 8.59 g of 2-hydroxyimino-2-(2-tritylamino-4-thiazolyl)-acetic acid in 10 ml of dioxane containing 4 mols of water per liter and 80 ml of dioxane were stirred under argon for 15 minutes to obtain suspension α. A solution of 5.134 g of potassium tert.-butylate in 40 ml of dioxane was stirred under argon at room temperature for 10 minutes to obtain a homogenous suspension and suspension α was added thereto over 15 minutes at 23°-25° C. The mixture was slowly cooled and was rinsed with 25 ml of dioxane. The mixture was stirred at 23°-25° C. for one hour and then a solution of 4.919 g of tert.-butyl bromoacetate in 15 ml of dioxane was added thereto over 15 minutes at 28°-29° C. The mixture was stirred at 26°-28° C. for one hour and then at a 10 minute interval, 0.471 g of potassium tert.-butylate and then a solution of 0.772 g of tert.-butyl bromoacetate in 2 ml of dioxane was added thereto. The mixture was stirred under argon at 25° C. for 45 minutes and the pH was adjusted to 6 with 0.5 ml of acetic acid. The mixture was evaporated to dryness to obtain 19.4 g of a resin which was taken up in 100 ml of methylene chloride and 100 ml of water. The pH of the mixture was acidified to 2-3 by addition of 25 ml of N hydrochloric acid and was decanted. The organic phase was washed with distilled water and was filtered. The aqueous phase was extracted with methylene chloride and the organic phase was dried, rinsed with methylene chloride and distilled to dryness under reduced pressure. The 12.3 g of residue were taken up in 31 ml of ethyl acetate and crystallization was started. The mixture was stirred for 1 hour at room temperature and then 2 hours at 0° to 5° C. and was vacuum filtered. The precipitate was rinsed with ethyl acetate at 0° to 5° C. and was dried under reduced pressure to obtain 5.04 g of product.

3.273 g of the said product were dissolved in 60 ml of refluxing methyl ethyl ketone saturated with water and 0.33 g of activated carbon were added to the hot mixture which was then vacuum filtered. The filter was rinsed twice with 3 ml of boiling methyl ethyl ketone saturated with water and the filtrate was concentrated under reduced pressure to remove 36 ml of solvent. A product crystallized while the mixture was iced at 0° to 5° C. for 1 hour with stirring and the mixture was vacuum filtered. The product was rinsed with methyl ethyl ketone saturated with water and was dried under reduced pressure to obtain 2.68 g of pure syn isomer of 2-tert.butyoxycarbonylmethyloxymino-2-(2-tritylamino-4-thiazolyl)-acetic acid melting at 190° C.

Analysis: $C_{30}H_{29}O_5N_3S$. Calculated: %C 66.28; %H 5.38; %N 7.73; %S 5.9. Found: 66.5; 5.7; 7.7; 5.6.

RMN (CDCl$_3$—60 MHz): 1.46 ppm (proton of tert.-butyl); 6.8 ppm (proton of thiazol ring).

STEP B: syn isomer of tert.-butyl 7-[2-(2-tritylamino-4-thiazolyl)-2-tert.-butoxycarbonylmethyloxyimino-acetamido]-3-acetoxymethyl-ceph-3-eme-4-carboxylate A mixture of 2.174 g of the product of Step A, 1.313 g of tert.-butyl 7-amino-cephalosporante and 35 ml of methylene chloride was stirred for 5 minutes at 20° C. and a solution of 8.8 ml of dicyclohexylcarbodiimide in methylene chloride (2.06 g per 20 ml) was added thereto over 5 minutes at 20°-22° C. The mixture was stirred under argon for 2 hours during which dicyclohexylurea precipitated and 4 drops of acetic acid were added thereto. The mixture was stirred for 5 minutes and was vacuum filtered. The filter was rinsed with methylene chloride to recover 523 mg of dicyclohexylurea and the filtrate was evaporated to dryness under reduced pressure. The residue was taken up in ether and was vacuum filtered to remove another 204 mg of dicyclohexylurea. 30 ml of ether were added to the filtrate and the mixture was washed with aqueous hydrochloride acid solution and then with water and aqueous sodium bicarbonate solution to recover in insoluble form 0.438 g of sodium 2-tert-butyoxycarbonylmethoxyimino-2-(2-tritylamino-4-thiazolyl)-acetate. The organic phase was washed with water until the wash waters were neutral and the wash waters were extracted with ether. The combined organic phases were dried, treated with activated carbon and vacuum filtered. The filtrate was rinsed with ether and the filtrate was evaporated to dryness under reduced pressure to obtain 3.16 g of product. The latter was chromatographed over silica gel and was eluted with a 1-1 ether-benzene mixture to obtain 1.15 g of first major fraction of the syn isomer of tert.-butyl 7-[2-(2-tritylamino-4-thiazolyl)-2-tert.-butoxycarbonylmethoxyimino-acetamido]-3-acetoxy methylceph-3-eme-4-carboxylate with an Rf=0.5 and 0.937 g of a homogenous second fraction with an Rf=0.5.

EXAMPLE 4 syn isomer of 7-[2-(2-amino-4-thiazolyl)-2-hydroxycarbonylmethoxyimino-acetamido]-3-acetoxymethyl-ceph-3-eme-4-carboxylic acid A mixture of 1.15 g of the product of Example 3 and 11.5 ml of trifluoroacetic acid was stirred under argon at 20°-22° C. for 10 minutes and mixture was concentrated to a volume of 3 ml. 35 ml of isopropyl ether were added to the mixture while cooling on an ice bath and the mixture was stirred for 10 minutes and was vacuum filtered. The product was rinsed with isopropyl ether and dried to obtain 0.557 g of trifluoroacetate and 0.526 g of said product was added to 2.5 ml of ethanol. The mixture was stirred at room temperature until dissolution occurred (pH-1-2) and a solution of 2 M pyridine in ethanol was added thereto. The free amine precipitated and the mixture was stirred under argon at 20°-25° C. for 5 minutes and was then vacuum filtered at room temperature. The recovered product was rinsed with a ether-ethanol-mixute and then with ether and dried to obtain 0.261 g of a yellow product. The mother liquors were concentrated to dryness and the residue was taken up in ether to obtain a second crop of 0.084 g of product. The combined products were empasted with an ethanol-ether mixture and then ether and dried to obtain 0.316 g of the syn isomer of 7-[2-(2-amino-4-thiazolyl)-2-hydroxycarbonylmethoxyimino-acetamido]-3-acetoxymethyl-ceph-3-eme-4-carboxylic acid.

RMN (DMSO—60 MHz): 4.16 ppm (O—C$\underline{H}$$_2$—COOH); 6.84 ppm (proton of thiazol ring).

EXAMPLE 5 syn isomer of disodium 7-[2-(2-amino-4-thiazolyl)-2-hydroxycarbonylmethoxyimino-acetamido]-3-acetoxymethyl-ceph-3-eme-4-carboxylate A solution of 0.224 g of the product of Example 4 in 1 ml of a methanolic solution of M sodium acetate and 2 ml of methanol was stirred and was vacuum filtered. The filter was rinsed with methanol and the filtrate was concentrated under reduced pressure to a volume of 1 ml. 5 ml of ethanol were added thereto to induce crystallization and the mixture was stirred at room temperature for 10 minutes and was vacuum filtered. The product was rinsed with ethanol and with ether and dried to obtain 200 mg of the syn isomer of disodium 7-[2-(2-amino-4-thiazolyl)-2-hydroxycarbonylmethyloxyimino-acetamido]-3-acetoxymethyl-ceph-3-eme-4-carboxylate with an Rf=0.3 (acetone with 10% water).

Analysis: $C_{17}H_{15}O_9N_5S_2Na_2$. Calculated: %Na 8.45. Found: 8.54.

EXAMPLE 6 syn isomer of tert.-butyl 7-[2-(2-tritylamino-4-thiazolyl)-2-cyanomethyloxyimino-acetamido]-3-acetoxymethyl-ceph-3-eme-4-carboxylate STEP A: syn isomer of cyanomethyl 2-(2-tritylamino-4-thiazolyl)-2-cyanomethyloxyimino-acetate A mixture of 12.9 g of the syn isomer of 2-(2-tritylamino-4-thiazolyl)-2-hydroxyimino-acetic acid, 9.12 g of neutral potassium carbonate, 60 ml of dry dimethylformamide and 7.6 ml of chloroacetonitrile was stirred under an inert atmosphere and after formation of a mass, the mixture stood for 65 hours under a closed atmosphere. The product was poured into a mixture of 750 ml of water, 130 ml of N hydrochloric acid and 150 ml of ethyl acetate and the mixture was stirred and vacuum filtered. The filter was rinsed with ethyl acetate and with water and the filtrate was decanted. The organic phase was washed with 100 ml of water and the aqueous phase was extracted 3 times with 100 ml of ethyl acetate. The combined organic phases were dried and were vacuum filtered. The filter was rinsed and the filtrate was evaporated to dryness and the residue was chromatographed over silica gel. Elution with ether yielded 8.69 g of the syn isomer of cyanomethyl 2-(2-tritylamino-4-thiazolyl)-2-cyanomethyloxyimino-acetate in the form of an oil.

RMN (CDCl$_3$—60 MHz): 6.8 ppm (proton of thiazole); 7.37 ppm (proton of trityl).

STEP B: syn isomer of 2-(2-tritylamino-4-thiazolyl)-2-cyanomethoxyimino-acetic acid A mixture of 8.69 g of the product of Step A in 52 ml of dioxane was cooled on an ice bath and 17.1 ml of N sodium hydroxide solution were added thereto dropwise over 20 minutes. Spontaneous heating occured and then 10.5 ml of 2 N hydrochloric acid were added thereto. The dioxane was distilled and only water remained as solvent. 20 ml of water and 30 ml of ether were added thereto and the mixture was stirred for 15 minutes and was vacuum filtered. The crystals were rinsed with water and ether and dried to obtain 4.32 g of the syn isomer of 2-(2-tritylamino-4-thiazolyl)-2-cyanomethoxyimino-acetic acid melting at about 180° C. with decomposition.

RMN (CDCl$_3$—60 MHz): 4.7 ppm (OCH$_2$—CN); 6.7 ppm (proton of thiazole); 7.34 ppm (proton of trityl).

STEP C: syn isomer of tert.-butyl 7-[2-(2-tritylamino-4-thiazolyl)-2-cyanomethoxyimino-acetamido]-3-acetoxymethyl-ceph-3-eme-4-carboxylate A mixture of 1.875 g of the product of Step A and 1.312 g of tert.-butyl 7-amino-cephalosponate in 12 ml of dry methylene chloride was stirred under an inert atmosphere and a solution of 960 mg of dicyclohexylcarbodiimide in 12 ml of dry methylene chloride was added thereto. The mixture was stirred and stood at room temperature for 105 minutes and was vacuum filtered to remove 457 mg of dicyclohexylurea. The filtrate was evaporated to dryness and the residue was chromatographed over silica gel. Elution was effected with methylene chloride and ether and the ether was evaporated. The product was taken up in ether and crystallization was induced. The mixture was slowly iced and was vacuum filtered. The recovered product was empasted at 0° C. with ether and was dried to obtain 776 mg of the syn isomer of tert-butyl 7-[2-(2-tritylamino-4-thiazolyl)-2-cyanomethyloxyimino-acetamido]-3-acetoxymethyl-ceph-3-eme-4-carboxylate melting at 180° C. with decomposition.

RMN (CDCl$_3$—60 MHz): 4.9 ppm (O—CH$_2$—CN); 6.8 ppm (proton of thiazole ring); 7.31 (proton of trityl).

EXAMPLE 7 trifluoroacetate of syn isomer of 7-[2-(2-amino-4-thiazolyl)-2-cyanomethyloxyimino-acetamido]-3-acetoxymethyl-ceph-3-eme-4-carboxylic acid A mixture of 779 mg of the product of Example 6 in 4 ml of trifluoroacetic acid was stirred until dissolution occured and the mixture was allowed to stand for 17 minutes. The mixture was poured into 40 ml of isopropyl ether and the mixture was stirred and vacuum filtered. The product was dried to obtain 523 mg of the trifluoroacetate of the syn isomer of 7-[2-(2-amino-4-thiazolyl)-2-cyanomethyloxyimino-acetamido]-3-acetoxymethyl-ceph-3-eme-4-carboxylic acid.

EXAMPLE 8 syn isomer of sodium 7-[2-(2-amino-4-thiazolyl)-2-cyanomethoxyimino-acetamido]-3-acetoxymethyl-ceph-3-eme-4-carboxylate 523 mg of the product of Example 7 were dissolved in 2 ml of a methanolic solution of N sodium acetate and the solution was diluted with 6.6 ml of ethanol. The mixture was stirred for 10 minutes and was vacuum filtered. The recovered product was rinsed with ethanol and dried to obtain 226 mg of the syn isomer of sodium 7-[2-(2-amino-4-thiazolyl)-2-cyanomethoxyimino-acetamido]-3-acetoxymethyl-ceph-3-eme-4-carboxylate melting at about 200° C. with decomposition.

RMN (CDCl$_3$—60 MHz): 4.98 ppm (O—CH$_2$—CN); 6.86 ppm (proton of thiazole ring).

Analysis: C$_{17}$H$_{15}$O$_7$N$_6$S$_2$Na. Calculated: %C 40.64; %H 3.01; %Na 4.57. Found: 40.2; 3.3; 4.5.

EXAMPLE 9 syn isomer of tert.-butyl 7-[2-(2-tritylamino-4-thiazolyl)-2-aminocarbonylmethyloxyimino-acetamido]-3-acetoxymethyl-ceph-3-eme-4-carboxylate STEP A: syn isomer of ethyl 2-(2-tritylamino-4-thiazolyl)-2-(ethylcarboxymethyloxyimino)-acetate 8.28 g of pure potassium carbonate were added under argon to a mixture of 9.88 g of the hydrochloride of ethyl 2-(2-tritylamino-4-thiazolyl)-2-hydroxyimino-acetate in 25 ml of dry dimethylformamide and the mixture was stirred for 15 minutes and was then cooled for 10 minutes on a methanol-ice bath. 11.2 ml of ethyl bromoacetate were added dropwise over 5 minutes and spontaneous heating occured with stirring under an inert atmosphere. The mixture was poured into a mixture of 400 ml of water and 80 ml of ethyl acetate and the mixture was stirred and decanted. The organic phase was washed twice with 80 ml of water and the aqueous phase was extracted with 80 and 50 ml of ethyl acetate. The organic phase was dried and vacuum filtered. The filter was rinsed and the filtrate was evaporated to dryness. The residue was taken up in ether and the mixture was stirred while crystallization occured. The mixture was vacuum filtered and the product was rinsed with ether and dried to obtain 7.54 g of syn isomer of ethyl 2-(2-tritylamino-4-thiazolyl)-2-(ethylcarboxymethyloxyimino)-acetate melting at 154° C.

RMN (CDCl$_3$—60 MHz): 4.75 ppm (O—CH$_2$—COO); 6.55 ppm (proton of thiazole ring).

Analysis: C$_{30}$H$_{29}$O$_5$N$_3$S. Calculated: %C 66.28; %H 5.38; %N 7.73; %S 5.90. Found: 66.1; 5.4; 7.5; 5.9.

STEP B: syn isomer of ethyl 2-(2-tritylamino-4-thiazolyl)-acetate-2-iminooxy-acetic acid A mixture of 4.077 g of the product of Step A in 11.3 ml of dioxane was cooled under an inert atmosphere in a bath of ice-water and 8.25 ml of N sodium hydroxide solution was added thereto over 20 minutes. The mixture was allowed to stand in the ice water bath for one hour and the dioxane was evaporated off at 25° C. 9.75 ml of N-hydrochloric acid were added thereto followed by the addition of 40 ml of ethyl acetate. The mixture was stirred and the organic phase was washed with water. The aqueous phase was extracted with ethyl acetate and the combined organic phases were dried over magnesium sulfate and were vacuum filtered. The filtrate was evaporated to dryness and the residue was taken up in ether. Crystallization started and the mixture was stirred for 30 minutes and then was vacuum filtered. The recovered product was rinsed with ether and dried to obtain 3.462 g of product melting at 200° C.

For analysis, 400 mg of the said product were dissolved in 1 ml of dioxane and the solution was diluted with 10 ml of isopropyl ether. The mixture was stirred and was cooled in a water ice bath to effect crystallization and was then vacuum filtered. The crystals were rinsed with isopropyl ether containing 10% of dioxane and were empasted with isopropyl ether to obtain 320 mg of the purified desired syn isomer.

RMN (CDCl$_3$—60 MHz): 4.71 ppm (O—CH$_2$—COO); 6.46 ppm (proton of thiazole ring).

STEP C: syn isomer of ethyl 2-(2-tritylamino-4-thiazolyl)-2-(aminocarbonylmethyloxyimino)-acetate A mixture of 3.609 g of the product of Step B, 28 ml of dry tetrahydrofuran, 21 ml of dry methylene chloride and 0.77 ml of pure N-methyl-morpholine was cooled under an inert atmosphere in a bath of dry ice and methanol until dissolution occured. After the dropwise addition of 0.91 ml of isobutyl chloroformate at −20° C., the mixture was stirred for 3 minutes at −20° C. and was cooled to −35° C. and then excess gaseous ammonia was added thereto at −20° C. The mixture was stirred for 15 minutes at −30° C. and then one hour at room temperature after which the mixture was evaporated to dryness. The residue was taken up in ethanol and the mixture was stirred for 20 minutes and was vacuum filtered. The recovered crystals were rinsed with ethanol and dried to obtain 3.33 g of the syn isomer of ethyl 2-(2-tritylamino-4-thiazolyl)-2-(aminocarbonylmethyloxyimino)-acetate melting at 180° C.

RMN (CDCl$_3$—60 MHz): 4.76 ppm (O—C$\underline{H}_2$—COO); 6.63 ppm (proton of thiazole ring).

Analysis: C$_{28}$H$_{26}$O$_4$N$_4$S. Calculated: %C 65.35; %H 5.09; %S 6.23. Found: 65.5; 5.1; 6.3.

STEP D: syn isomer of 2-(2-tritylamino-4-thiazolyl)-2-(aminocarbonylmethyloxyimino)-acetic acid A mixture of 3.5 g of the product of Step C, 24 ml of dioxane and 6.8 ml of 2 N sodium hydroxide was stirred at room temperature until dissolution occured and the mixture stood for 45 minutes during which crystallization occured. The mixture was stirred in a sealed atmosphere for 3¼ hours and was then vacuum filtered. The recovered sodium salt was rinsed with a 7-3 dioxane-water mixture and then with ether and was dried to obtain 1.81 g of the sodium salt which was then dissolved in 5.3 ml of dimethylsulfoxide. 5 ml of N hydrochloric acid solution were added to the solution which caused a precipitation and then crystallization and the 70 ml of water were added thereto. The mixture was stirred for 20 minutes and was then vacuum filtered. The recovered product was rinsed with water and dried to obtain 1.3 g of the syn isomer of 2-(2-tritylamino-4-thiazolyl)-2-(aminocarbonylmethyloxyimino)-acetic acid melting at ≃200° C.

RMN (CDCl$_3$—60 MHz): 4.58 ppm (O—C$\underline{H}_2$—CO); 6.66 ppm (proton of thiazole ring).

STEP E: syn isomer of tert.-butyl 7-[2-(2-tritylamino-4-thiazolyl)-2-(aminocarbonylmethyloxyimino)-acetamido]-3-acetoxymethyl-ceph-3-eme-4-carboxylate A solution of 240 mg of dicyclohexylcarbodiimide in 3 ml of dry methylene chloride was added at room temperature under an inert atmosphere to a mixture of 488 mg of the product of Step D, 328 mg of tert.-butyl 7-amino-cephalosponate and 3 ml of dry methylene chloride and after dissolution occured, crystals began to appear. The mixture was stirred for 2 hours and was vacuum filtered to remove dicyclohexylurea formed which was rinsed with methylene chloride and dried to obtain 130 mg. The filtrate was evaporated to dryness and the residue was chromatographed over silica gel. Elution was effected with a 7-2-1 ethyl acetate-ethanol-water mixture and the solution was evaporated to dryness. The residue was taken up in 1 ml of ethanol and the solution was diluted with isopropyl ether which caused a precipitate to form. The mixture was vacuum filtered and the product was rinsed with an 89-11 isopropyl ether-ethanol mixture, was empasted with isopropyl ether and dried to obtain 324 mg of the syn isomer of tert.-butyl 7-[2-(2-tritylamino-4-thiazolyl)-2-(aminocarbonylmethyloxyimino)-acetamido]-3-acetoxymethyl-ceph-3-eme-4-carboxylate.

RMN Spectrum (CDCl$_3$—60 MHz): 6.68 ppm (proton of thiazole ring).

EXAMPLE 10 trifluoroacetate of syn isomer of 7-[2-(2-amino-4-thiazolyl)-2-(aminocarbonylmethyloxyimino)-acetamido]-3-acetoxymethyl-ceph-3-eme-4-carboxylic acid A solution of 357 ml of the product of Example 9 in 11 ml of trifluoroacetic acid stood in a closed atmosphere for 25 minutes and 11 ml of isopropyl ether were then added thereto to cause precipitation. The mixture was vacuum filtered and the product was rinsed with isopropyl ether and dried to obtain 275 mg of the trifluoroacetate of the syn isomer of 7-[2-(2-amino-4-thiazolyl)-2-(aminocarbonylmethyloxyimino)-acetamido]-3-acetoxymethyl-ceph-3-eme-4-carboxylic acid.

EXAMPLE 11 syn isomer of sodium 7-[2-(2-amino-4-thiazolyl)-2-(aminocarbonylmethoxyimino)-acetamido]-3-acetoxymethyl-ceph-3-eme-4-carboxylate A solution of 275 mg of the trifluoroacetate of Example 10 in 1.2 ml of a methanolic 1 M sodium acetate solution was diluted with 4 ml of ethanol to effect precipitation and the mixture was vacuum filtered. The product was rinsed with ethanol and dried to obtain 153 mg of the syn isomer of sodium 7-[2-(2-amino-4-thiazolyl)-2-(aminocarbonylmethyloxyimino)-acetamido]-3-acetoxymethyl-ceph-3-eme-4-carboxylate melting at about 200° C. with decomposition.

RMN Spectrum (CDCl$_3$—90 MHz): 4.4 ppm (=N—OC$\underline{H}_2$—CO); 6.8 ppm (proton of thiazole ring).

EXAMPLE 12 syn isomer of tert.-butyl 7-[2-(2-tritylamino-4-thiazolyl)-2-(1-tert.-butoxycarbonyl-1-methylethyloxyimino)-acetamido]-3-acetoxymethyl-ceph-3-eme-4-carboxylate STEP A: syn isomer of ethyl 2-(2-tritylamino-4-thiazolyl)-2-(1-tert.-butoxycarbonyl-1-methylethyloxyimino)-acetate A mixture of 9.88 g of the hydrochloride of ethyl 2-(2-tritylamino-4-thiazolyl)-2-hydroxyimino-acetate and 8.28 g of potassium carbonate in 25 ml of dry dimethylformamide was cooled in a bath at −10° C. for 10 minutes and 19 ml of raw tert.-butyl 2-bromo-2-methyl-propionate were added thereto over 3 minutes. The mixture was stirred for 16 hours during which it solidifed into a mass which was poured into a mixture of 400 ml of distilled water and 200 ml of ethyl acetate. The mixture was stirred and decanted and the organic phase was washed with water. The aqueous phase was extracted twice with 100 ml of ethyl acetate and the combined organic phases were dried and vacuum filtered. The filtrate was evaporated to dryness to obtain an oil residue which was added to 240 ml of petroleum ether. The mixture was cooled and crystallization was effected. The mixture was vacuum filtered after 30 minutes to obtain 10.8 g of the syn isomer of ethyl 2-(2-tritylamino-4-thiazolyl)-2-(1-tert.-butoxycarbonyl-1-methylethyl oxyimino)-acetate melting at 134° C.

RMN Spectrum (CDCl$_3$—60 MHz): 6.71 ppm (proton of thiazole ring); 7.28 ppm (trityl proton).

Analysis: $C_{34}H_{37}O_5N_3S$. Calculated: %C 68.09; %H 6.22; %N 7.01; %S 5.35. Found: 68.3; 6.3; 6.9; 5.3.

STEP B: syn isomer of 2-(2-tritylamino-4-thiazolyl)-2-(1-tert.-butoxycarbonyl-1-methylethyloxyimino)-acetic acid A mixture of 1.2 g of the product of Step A, 2 ml of methanolic 1 N potassium hydroxide solution and 4 ml of methanol was refluxed for 2 hours and was then cooled during which 390 mg of the starting material crystallized which meant 810 mg of the starting product was saponified. The mixture was filtered and the filtrate was evaporated to dryness. The residue was taken up in 1 ml of dimethylformamide and 2 ml of N hydrochloric acid solution (pH=2). The mixture was stirred and 10 ml of water were added thereto. The mixture was extracted with methylene chloride and the organic phase was washed with water. The wash waters were extracted with methylene chloride and the combined organic phases were dried and vacuum filtered. The filtrate was evaporated and the oil residue was taken up in 4 ml of chloroform. The solution was diluted with 30 ml of ether and crystallization was effected. After 30 minutes with stirring, the mixture was vacuum filtered and the product was rinsed with ether and dried to obtain 472 mg of the syn isomer of 2-(2-tritylamino-4-thiazolyl)-2-(1-tert.-butoxycarbonyl-1-methylethyloxyimino)-acetic acid melting at 190° C.

RMN Spectrum (DMSO—60 MHz): 6.76 ppm (proton of thiazole ring); 7.33 ppm (trityl proton)

STEP C: syn isomer of tert.-butyl 7-[2-(2-tritylamino-4-thiazolyl)-2-(1-tert.-butoxycarbonyl-1-methylethyloxyimino)-acetamido]-3-acetoxymethyl-ceph-3-eme-4-carboxylate A mixture of 1.715 g of the product of Step B, 984 mg of tert.-butyl 7-amino-cephalosponate and 26 ml of methylene chloride was heated to effect dissolution and was then cooled to room temperature. 678 mg of dicyclohexylcarbodiimide in 6.6 ml of dry methylene chloride were added thereto and the mixture was stirred at room temperature for 2 hours during which dicyclohexylurea crystallized. The mixture was vacuum filtered to remove 268 mg of said urea and the filtrate was evaporated to dryness. The residue was taken up in either and a little acetic acid was added thereto to adjust the pH to 4. The mixture was stirred for 20 minutes and was vacuum filtered. The filter was rinsed with ether to remove another 79 mg of dicyclohexylurea and the filtrate was evaporated to dryness. The residue was chromatographed over silica gel and was eluted with ether to obtain 463 mg of the syn isomer of tert.-butyl 7-[2-(2-tritylamino-4-thiazolyl)-2-(1-tert.-butoxycarbonyl-1-methylethyloxyimino)-acetamido]-3-acetoxymethyl-ceph-3-eme-4-carboxylate with Rf=0.7 (ether eluant).

EXAMPLE 13 trifluoroacetate of the syn isomer of 7-[2-(2-amino-4-thiazolyl)-2-(1-carboxy-1-methylethyloxyimino)-acetamido]-3-acetoxymethyl-ceph-3-eme-4-carboxylic acid A mixture of 432 mg of the product of Example 12 and 4.3 ml of pure trifluoroacetic acid stood for 15 minutes until dissolution occured and 43 ml of isopropyl ether were added thereto. The mixture was vacuum filtered and the solvent was evaporated. The residue was taken up in 50 ml of isopropyl ether and the mixture was vacuum filtered. The product was rinsed with isopropyl ether to obtain 173 mg of the trifluoroacetate of the syn isomer of 7-[2-(2-amino-4-thiazolyl)-2-(1-carboxy-1-methylethyloxyimino)-acetamido]-3-acetoxymethyl-ceph-3-eme-4-carboxylic acid with an Rf=0.5 (acetone containing 10% water as diluent).

EXAMPLE 14 syn isomer of disodium 7-[2-(2-amino-4-thiazolyl)-2-(1-carboxy-1-methylethoxyimino)-acetamido]-3-acetoxymethyl-ceph-3-eme-4-carboxylate A mixture of 173 mg of the product of Example 13 and 0.95 ml of a methanolic 1 M sodium acetate solution was slightly heated and filtered to remove insolubles. The filter was rinsed and the filtrate was reduced to a small volume. The mixture was diluted with 2.5 ml of ethanol and was stirred and vacuum filtered. The product was rinsed with ethanol and then with ether and dried to obtain 77 mg of the syn isomer of disodium 7-[2-(2-amino-4-thiazolyl)-2-(1-carboxy-1-methylethyloxyimino)-acetamido]-3-acetoxymethyl-ceph-3-eme-4-carboxylate.

RMN Spectrum (DMSO—60 MHz): 6.75 ppm (proton of thiazole ring).

Analysis: $C_{19}H_{19}O_9N_5S_2Na_2$. Calculated: %C 39.93; %H 3.35. Found: 39.5; 3.6.

EXAMPLE 15 syn isomer of diphenylmethyl 7-[2-(2-tritylamino-4-thiazolyl)-2-(tert.-butoxycarbonylmethoxyimino)-acetamido]-3-acetoxymethyl-ceph-3-eme-4-carboxylate STEP A: syn isomer of 2-(2-tritylamino-4-thiazolyl)-2-(1-methyl-1-methoxylethoxyimino)-acetic acid A mixture of 12.9 g of the syn isomer of 2-(2-tritylamino-4-thiazolyl)-2-hydroxyimino-acetic acid, 120 ml of methylene chloride and 12 ml of 2-methoxypropene was stirred for 20 minutes at room temperature and was then evaporated to dryness. The residue was stirred for another 30 minutes in 60 ml of methylene chloride and 12 ml of 2-methoxypropene and the mixture was evaporated to dryness under reduced pressure to obtain the syn isomer of 2-(2-tritylamino-4-thiazolyl)-2-(1-methyl-1-methoxyethoxyimino)-acetic acid which was used as is for the next step.

STEP B: syn isomer of diethylamine 7-[2-(2-tritylamino-4-thiazolyl)-2-(1-methyl-1-methoxyethoxyimino-acetamido]-3-acetoxymethyl-ceph-3-eme-4-carboxylate 12.5 g of dicyclohexylcarbodiimide were added to a solution of the product of Step A starting rom 47.25 g of the hydroxyimino-acetic acid in 230 ml of methylene chloride and the mixture was stirred at room temperature for one hour and was vacuum filtered. The dicyclohexylurea was rinsed with a small amount of methylene chloride (9.82 g of solid) and the filtrate was cooled to a solution of 13.6 g of 7-amino-cephalosporanic acid in 70 ml of methylene chloride and 14 ml of triethylamine. The mixture was stirred for 2 hours at room temperature and was washed in a flask with 350 ml of N hydrochloric acid. The organic phase was decanted and washed with water, dried and evaporated to dryness. The residue was dissolved in 100 ml of ethyl acetate and crystallization was induced. The mixture stood for 30 minutes and was then vacuum filtered to recover 5.5 g of the starting material. The filtrate was evaporated to dryness and a mixture of the residue and 200 ml of isopropyl ether was stirred for 30 minutes and was then vacuum filtered. The product was dried to obtain 37.35 g of raw product. The latter was dissolved in 148 ml of ethyl acetate and 5.5 ml of diethylamine were added to the solution. The mixture was stirred with 650 ml of ether to induce crystallization and was then vacuum filtered. The product was washed with ether and dried to obtain 26.35 g of product. The filtrate was evaporated to dryness and the residue was taken up in ether to obtain a second yield of 2.8 g of product identical to the first product of the syn isomer of diethylamine 7-[2-(2-tritylamino-4-thiazolyl)-2-(1-methyl-1-methoxyethoxyimino)-acetamido]-3-acetoxymethyl-ceph-3-eme-4-carboxylate.

RMN Spectrum (CDCl$_3$—60 MHz):

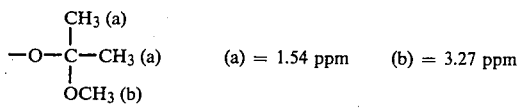

6.78 ppm (proton of thiazole ring).

STEP C: syn isomer of diphenylmethyl 7-[2-(2-tritylamino-4-thiazolyl)-2-(1-methyl-1-methoxyethoxyimino)-acetamido]-3-acetoxymethyl-ceph-3-eme-4-carboxylate A mixture of 4.15 g of the salt of Step B, 40 ml of methylene chloride and 55 ml of 0.1 N hydrochloric acid was stirred for 10 minutes at room temperature and the organic phase was decanted and washed twice with 25 ml of water, dried and vacuum filtered. The product was rinsed with methylene chloride and was added over 10 minutes with stirring to 15 ml of 8% diazodiphenylmethane in benzene. The mixture was stirred for 15 minutes at room temperature and was evaporated to dryness at 30° C. under reduced pressure. The residue was taken up in isopropyl ether and efflorescence occured. The solvent was evaporated under reduced pressure and the residue was again taken up in isopropyl ether and vacuum filtered. The product was rinsed and dried to obtain 4.41 g of the syn isomer of diphenylmethyl 7-[2-(2-tritylamino-4-thiazolyl)-2-(1-methyl-1-methoxyethoxyimino)-acetamido]-3-acetoxymethyl-ceph-3-eme-4-carboxylate.

RMN Spectrum (CDCl$_3$—60 MHz):

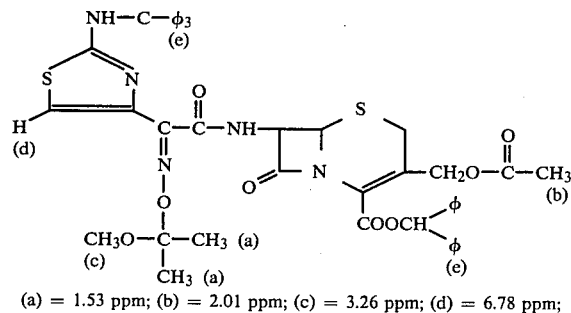

(a) = 1.53 ppm; (b) = 2.01 ppm; (c) = 3.26 ppm; (d) = 6.78 ppm; (e) = 7.33 ppm.

STEP D: syn isomer of diphenylmethyl 7-[2-(2-tritylamino-4-thiazolyl)-2-hydroxyimino-acetamido]-3-acetoxymethyl-ceph-3-eme-4-carboxylate A mixture of 2.775 g of the product of Step C, 14 ml of acetone and 4.5 ml of N hydrochloric acid was stirred for 2 hours at room temperature and the acetone was evaporated under reduced pressure. 20 ml of ethyl acetate were added thereto and the mixture was stirred and decanted. The organic phase was washed 4 times with 10 ml of slightly salted water and the wash waters were extracted with 5 ml of ethyl acetate. The combined organic phases were dried and vacuum filtered and the filter was rinsed with ethyl acetate. The filtrate was evaporated to dryness under reduced pressure and the residue was taken up in ether. Crystallization and efflorescence occured and the mixture was vacuum filtered. The product was rinsed with ether and dried to obtain 1.88 g of the syn isomer of diphenylmethyl 7-[2-(2-tritylamino-4-thiazolyl)-2-hydroxyimino-acetamido]-3-acetoxymethyl-ceph-3-eme-4-carboxylate with Rf=0.5 (ether containing 20% of acetone).

RMN Spectrum (CDCl$_3$—60 MHz): 6.88 ppm (proton of thiazole ring); 7.33 ppm (proton of phenyl rings).

STEP E: syn isomer of diphenylmethyl 7-[2-(2-tritylamino-4-thiazolyl)-2-(tert.-butoxycarbonylmethyloxyimino)-acetamido]-3-acetoxymethyl-ceph-3-eme-4-carboxylate A mixture of 0.85 g of the product of Step D, 0.8 ml of tert.-butyl bromoacetate and 4 ml of dimethylformamide stood in an ice bath for 5 minutes and then 1.7 g of silver oxide were added thereto. The mixture was stirred for one hour after removal of the bath and the mixture was vacuum filtered. The filter was rinsed with ethyl acetate and 80 ml of water were added to the filtrate which was decanted. The aqueous phase was extracted twice with 20 ml of ethyl acetate and the combined organic phases were washed twice with 50 ml of aqueous sodium chloride solution, dried, treated with 80 mg of activated carbon and vacuum filtered. The filter was rinsed with ethyl acetate and the filtrate was evaporated to dryness under reduced pressure. The residue was taken up in isopropyl ether and after efflorescence, the mixture was vacuum filtered. The product was rinsed with isopropyl ether and dried to obtain 0.724 g of the syn isomer of diphenylmethyl 7-[2-(2-tritylamino-4-thiazolyl)-2-(tert.-butoxycarbonylmethyloxyimino)-acetamido]-3-acetoxymethyl-ceph-3-eme-4-carboxylate with Rf=0.34 (methylene chloride containing 5% of ether).

EXAMPLE 16 trifluoroacetate of the syn isomer of 7-[2-(2-amino-4-thiazolyl)-2-carboxymethyloxyimino-acetamido]-3-acetoxymethyl-ceph-3-eme-4-carboxylic acid 0.482 g of the product of Example 16 were added to 5 ml of trifluoroacetic acid cooled on an ice-methanol bath and the mixture was stirred for 15 minutes after removal from the bath and dissolution occured in 5 minutes. The acid was evaporated under reduced pressure and 20 ml of isopropyl ether were added to the mixture which then stirred for 5 minutes and was filtered. The product was rinsed with isopropyl ether and dried to obtain 0.277 g of the trifluoroacetate of the syn isomer of 7-[2-(2-amino-4-thiazolyl)-2-carboxylmethyloxyimino-acetamido]-3-acetoxymethyl-ceph-3-eme-4-carboxylic acid identical to the product of Example 4.

EXAMPLE 17 syn isomer of disodium 7-[2-(2-amino-4-thiazolyl)-2-carboxylmethyloxyimino-acetamido]-3-acetoxymethyl-ceph-3-eme-4-carboxylate 1.5 ml of a methanol solution of M sodium acetate was slowly added to a solution of the product of Example 16 in 0.5 ml of methanol and after efflorescence, 5 ml of ethanol were slowly added thereto. The mixture was vacuum filtered and the recovered product was rinsed twice with ethanol, then with ether and dried to obtain 0.178 g of the syn isomer of disodium 7-[2-(2-amino-4-thiazolyl)-2-carboxymethyloxyimino-acetamido]-3-acetoxymethyl-ceph-3-eme-4-carboxylate identical to the product of Example 5.

EXAMPLE 18 syn isomer of tert.-butyl 7-[2-(2-tritylamino-4-thiazolyl)-2-(tert.-butoxycarbonyl-methyloxyimino)-acetamido]-3-acetoxymethyl-ceph-3-eme-4-carboxylate STEP A: syn isomer of tert.-butyl 7-[2-(2-tritylamino-4-thiazolyl)-2-(1-methyl-1-methoxyethoxyimino)-acetamido]-3-acetoxymethyl-ceph-3-eme-4-carboxylate 9.84 g of tert.-butyl 7-amino-cephalosporonate were added to a solution of the product of Step A of Example 15 in 120 ml of methylene chloride and after cooling the mixture to 10° C., 6.6 g of dicyclohexylcarbodiimide were added thereto. The mixture was cooled in an ice bath and was then stirred at room temperature for 3 hours and was then vacuum filtered to remove 4 g of dicyclohexylurea. The filtrate was evaporated to dryness and the residue was dissolved in 25 ml of ethyl acetate. 100 ml of ether were added and the organic phase was washed with 100 ml of 0.2 N hydrochloric acid, 100 ml of water and 20 ml of 1 M sodium bicarbonate solution. The mixture was vacuum filtered and dried to obtain 3.9 g of the recovered sodium salt. The salt was washed with water, dried and vacuum filtered. The filtrate was evaporated to dryness and the residue was taken up in 50 ml of isopropyl ether. Crystallization was induced by addition of 50 ml of isopropyl ether and was vacuum filtered. The precipitate was washed and dried to obtain 10.8 g of the syn isomer of tert.-butyl 7-[2-(2-tritylamino-4-thiazolyl)-2-(1-methyl-1-methoxyethoxyimino)-acetamido]-3-acetoxymethyl-ceph-3-eme-4-carboxylate melting at ≃160° C.

RMN Spectrum (CDCl$_3$—60 MHz):

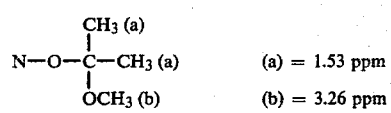

6.76 ppm (proton of thiazole ring).

STEP B: syn isomer of tert.-butyl 7-[2-(2-tritylamino-4-thiazolyl)-2-hydroxyimino-acetamido]-3-acetoxymethyl-ceph-3-eme-4-carboxylate A solution of 0.812 g of the product of Step A, 4 ml of acetone and 1 ml of N hydrochloric acid was stirred at room temperature for 3 hours and 1 ml of an aqueous solution of 1 M sodium bicarbonate, 10 ml of water and 5 ml of ethyl acetate were added thereto to obtain 0.551 g of the syn isomer of tert.-butyl 7-[2-(2-tritylamino-4-thiazolyl)-2-hydroxyimino-acetamido]-3-acetoxymethyl-ceph-3-eme-4-carboxylate melting at ≃200° C.

Analysis: $C_{38}H_{37}O_7N_5S_2$. Calculated: %C 61.69; %H 5.04; %N 9.47; %S 8.66. Found: 61.5; 5.0; 9.1; 8.4.

RMN Spectrum (CDCl$_3$—60 MHz): 1.55 ppm (tert.-butyl); 6.88 ppm (proton of thiazole ring).

STEP C: syn isomer of tert.-butyl 7-[2-(2-tritylamino-4-thiazolyl)-2-tert.-butoxycarbonylmethyloxyimino)-acetamido]-3-acetoxymethyl-ceph-3-eme-4-carboxylate 0.5 g of silver oxide were added at 20° C. to a mixture of 0.074 g of the product of Step B, 0.7 ml of dimethylformamide and 0.5 ml of tert.-butyl bromoacetate and the mixture was stirred for 30 minutes and was vacuum filtered. The filter was rinsed with ethyl acetate and the filtrate was added to 10 ml of water. The mixture was decanted and the aqueous phase was extracted with 5 ml of ethyl acetate. The combined organic phases were washed with 5 ml of aqueous sodium chloride solution, dried over magnesium sulfate and was vacuum filtered. The filter was rinsed with ethyl acetate and the filtrate was evaporated to dryness. The residue was taken up in isopropyl ether and efflorescenced. The mixture was vacuum filtered and the product was rinsed with isopropyl ether and dried to obtain 0.02 g of the syn isomer of tert.-butyl 7-[2-(2-tritylamino-4-thiazolyl)-2-(tert.-butoxycarbonylmethoxyimino)-acetamido]-3-acetoxymethyl-ceph-3-eme-4-carboxylate with Rf=0.34 (methylene chloride containing 5% ether). The product was identical to the product of Example 3.

EXAMPLE 19 syn isomer of diethylamine 7-[2-(2-tritylamino-4-thiazolyl)-2-(tert.-butoxycarbonyl-methyloxyimino)-acetamido]-3-acetoxymethyl-ceph-3-eme-4-carboxylate STEP A: syn isomer of diethylamine 7-[2-(2-tritylamino-4-thiazolyl)-2-hydroxyimino-acetamido]-3-acetoxymethyl-ceph-3-eme-4-carboxylate A salt of 7.6 g of the diethylamine salt of Step B of Example 15 in 30 ml of acetone and 10 ml of 2 N hydrochloric acid was stirred for 40 minutes at room temperature and then 20 ml of water were added thereto. The acetone was evaporated at 30° C. under reduced pressure and 25 ml of ethyl acetate were added thereto. The organic phase was decanted, reextracted and was washed with water and dried. The mixture was vacuum filtered and 1 ml of diethylamine was added to the filtrate. The mixture was triturated, iced and vacuum filtered. The product was washed with ether to obtain 6 g of pure syn isomer of diethylamine 7-[2-(2-tritylamino-4-thiazolyl)-2-hydroxyimino-acetamido]-3-acetoxymethyl-ceph-3-eme-4-carboxylate.

Analysis: $C_{38}H_{40}O_7N_6S_2$. Calculated: %C 60.30; %H 5.33; %N 11.10; %S 8.47. Found: 60.5; 5.7; 10.9; 8.2.

RMN Spectrum (CDCl$_3$=60 MHz): 6.63 ppm (proton of thiazole ring); 7.33 ppm (proton of trityl).

STEP B: syn isomer of diethylamine 7-[2-(2-tritylamino-4-thiazolyl)-2-(tert.-butoxycarbonylmethyloxyimino)-acetamido]-3-acetoxymethyl-ceph-3-eme-4-carboxylate The salt of Step A was dissolved in methylene chloride and aqueous hydrochloric acid was added thereto and the residue was redissolved in isopropyl ether to obtain 10.25 g of the corresponding free acid which was then dissolved in 225 ml of methylene chloride. 150 ml of distilled water were added thereto and 21 ml of triethylamine were added thereto with stirring to form an emulsion. 13.2 ml of tert.-butyl bromoacetate were added thereto and the mixture was stirred for 3½ hours at 20°–25° C. The mixture was acidified by addition of 90 ml of 2 N hydrochloric acid at 15° to 20° C. and the mixture was stirred and decanted. The organic phase was washed with distilled water and the wash waters were extracted with chloroform. The combined organic phases were dried and vacuum filtered and the filter was rinsed with methylene chloride. The filtrate was evaporated to dryness to obtain 14.85 g of a brown resin which was taken up in 30 ml of acetate. 1.65 ml of diethylamine were slowly added thereto at 20° C. and the solution was added with stirring over 10 minutes to a balloon flask containing 60 ml of isopropyl ether. The mixture was stirred for 30 minutes at 20°–25° C. and was then vacuum filtered. The product was rinsed twice with 5 ml of a 1-2 ethyl acetate-isopropyl ether mixture and then with isopropyl ether and was dried to obtain 11.14 g of product. The filtrate was added to 30 ml of ethyl acetate containing 10% of isopropyl ether which caused a precipitate to occur and the mixture was stirred for 5 minutes and was vacuum filtered. The filtrate was evaporated to dryness and the brown residue was taken up in 50 ml of isopropyl ether. The mixture was stirred for one hour at room temperature and was vacuum filtered. The product was rinsed with isopropyl ether to obtain 10.75 g of the syn isomer of diethylamine 7-[2-(2-tritylamino-4-thiazolyl)-2-(tert.-butoxycarbonylmethyloxyimino)-acetamido]-3-acetoxymethyl-ceph-3-eme-4-carboxylate.

Analysis: $C_{44}H_{50}O_9N_6S_2$. Calculated: %C 60.67; %H 5.78; %N 9.65; %S 7.36. Found: 61.1; 5.8; 9.6; 7.1.

RMN Spectrum ($CDCl_3$ 13 60 MHz): 1.43 ppm (tert.-butyl); 6.8 ppm (proton of thiazole ring).

EXAMPLE 20 trifluoroacetate of syn isomer of 7-[2-(2-amino-4-thiazolyl)-2-carboxymethyloxyimino-acetamido]-3-acetoxymethyl-ceph-3-eme-4-carboxylic acid 9 g of the salt of Example 19 were added over one minute under an inert atmosphere at 20°–25° C. to 36 ml of trifluoroacetic acid and the mixture was stirred for 15 minutes under an inert atmosphere. The mixture was cooled on an ice water bath and 360 ml of isopropyl ether were rapidly added thereto. The mixture was stirred for 15 minutes and was vacuum filtered and the product was rinsed with isopropyl ether, then ether and dried to obtain 5.08 g of raw product. 8.28 g of raw product from different runs were empasted for 15 minutes with 33 ml of acetone containing 1% of water and the mixture was diluted with 330 ml of ethanol. The mixture was stirred for 15 minutes and was vacuum filtered and the product was rinsed with ether and dried to obtain 7.03 g of the trifluoroacetate of the syn isomer of 7-[2-(2-amino-4-thiazolyl)-2-carboxymethyloxyimino)-acetamido]-3-acetoxymethyl-ceph-3-eme-4-carboxylic acid which was identical to the product of Example 16.

EXAMPLE 21

Injectable preparations were prepared with 500 mg of the syn isomer of 7-[2-(2-amino-4-thiazolyl)-2-(carbethoxymethyloxyimino)-acetamido]-3-acetoxymethyl-ceph-3-eme-4-carboxylic acid or the syn isomer of the disodium salt of 7-[2-(2-amino-4-thiazolyl)-2-(hydroxycarbonylmethyloxyimino)-acetamido]-3-acetoxymethyl-ceph-3-eme-4-carboxylic acid or the syn isomer of sodium 7-[2-(2-amino-4-thiazolyl)-2-(cyanomethyloxyimino)-acetamido]-3-acetoxymethyl-ceph-3-eme-4-carboxylate or the syn isomer of sodium 7-[2-(2-amino-4-thiazolyl)-2-(aminocarbonylmethyloxyimino)-acetamido]-3-acetoxymethyl-ceph-3-eme-4-carboxylate and sufficient sterile water for a final volume of 5 ml. Also prepared were gelules containing 250 mg of the syn isomer of disodium 7-[2-(2-amino-4-thiazolyl)-2-hydroxycarbonylmethyloxyimino-acetamido]-3-acetoxymethyl-ceph-3-eme-4-carboxylate or the sym isomer of the sodium salt of 7-[2-(2-amino-4-thiazolyl)-2-(cyanomethyloxyimino)-acetamido]-3-acetoxymethyl-ceph-3-eme-4-carboxylic acid and sufficient excepient for a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 or 48 hours at 37° C. in an oven. The increasing inhibition was determined by transillumination to determine the minimum inhibiting concentration (MIC in μg/ml) and the results are reported in the following Tables.

| STRAIN | Product of Example 2 MIC in μg/ml 24 H | 48 H | Product of Example 5 MIC in μg/ml 24 H | 48 H |
|---|---|---|---|---|
| Staphylococcus aureus ATCC 6 538 Pen-Sensible | 3 | 5 | 10 | 10 |
| Staphylococcus aureus UC 1 128 Pen-Resistant | 3 | 3 | 20 | 20 |
| Staphylococcus aureus exp. n° 54 146 | 3 | 5 | 20 | 20 |
| Streptococcus pyogenes A 561 | 0,05 | 0,1 | 0,5 | 0,5 |
| Streptococcus faecalis 5 432 | 5 | >40 | 20 | >40 |
| Streptococcus faecalis 99 F 74 | >40 | >40 | >40 | >40 |
| Bacillus subtilis ATCC 6 633 | 0,5 | 5 | | |
| Escherichia Coli Sensible Tetracycline ATCC 9 637 | 2 | 2 | 0,2 | 0,2 |
| Escherichia Coli Resistant Tetracycline ATCC 11 303 | 0,5 | 1 | 0,05 | 0,05 |
| Escherichia Coli Exp. $TO_{26}B_6$ | 1 | 1 | 0,1 | 0,1 |
| Escherichia Coli Resistant Gentamicine, Tobramycine R 55 123 D | 1 | 1 | 0,1 | 0,1 |
| Klebsiella pneumoniae Exp. 52 145 | 0,1 | 0,2 | 0,1 | 0,1 |
| Klebsiella pneumoniae 2 536 Resistant Gentamicine | 2 | 2 | 0,1 | 0,1 |
| Proteus vulgaris (indol +) A 232 | 1 | 1 | 0,1 | 0,1 |
| Proteus mirabilis (indol −) A 235 | 0,2 | 0,2 | ≦0,02 | ≦0,02 |
| Salmonella typhimurium 420 | 1 | 2 | 0,2 | 0,5 |
| Enterobacter cloacae 681 | 10 | 10 | 5 | 20 |
| Providencia Du 48 | 5 | 5 | 1 | 2 |
| Serratia Resistant Gentamicine 2 532 | 5 | 5 | 1 | 2 |

| PRODUCT OF EXAMPLE 8 | | |
|---|---|---|
| STRAIN | MIC in μg/ml 24 H | 48 H |
| Staphylococcus aureus ATCC 6 538 Pen-Sensible | 2 | 2 |
| Staphylococcus aureus UC 1 128 Pen-Resistant | 2 | 3 |
| Staphylococcus aureus exp. n° 54 146 | 2 | 3 |
| Streptococcus pyogenes A 561 | 0,05 | 0,05 |
| Streptococcus faecalis 5 432 | 3 | 20 |
| Streptococcus faecalis 99 F 74 | 10 | >40 |
| Bacillus subtilis ATCC 6 633 | 0,5 | 1 |
| Escherichia-Coli Sensible Tetracycline ATCC 9 637 | 0,5 | 0,5 |

PRODUCT OF EXAMPLE 8

| STRAIN | MIC in μg/ml | |
|---|---|---|
| | 24 H | 48 H |
| *Escherichia Coli* Resistant Tetracycline ATCC 11 303 | 0,05 | 0,05 |
| *Escherichia Coli* Exp. $TO_{26}B_6$ | 0,2 | 0,2 |
| *Esherichia Coli* Resistant Gentamicine, Tobramycine R 55 123 D | 0,2 | 0,2 |
| *Klebsiella pneumoniae* Exp. 52 145 | 0,05 | 0,05 |
| *Klebsiella pneumoniae* 2 536 Resistant Gentamycine | 1 | 1 |
| *Proteus mirabilis* (indol −) A 235 | 0,05 | 0,05 |
| *Salmonella typhimurium* 420 | 0,5 | 0,5 |
| *Enterobacter cloacae* 681 | 3 | 5 |
| *Providencia Du* 48 | 5 | 5 |
| *Serratia* Resistant Gentamicine 2 532 | 2 | 2 |

PRODUCT OF EXAMPLE 11

| STRAIN | MIC in μg/ml | |
|---|---|---|
| | 24 H | 48 H |
| *Staphylococcus aureus* ATCC 6 538 Pen-Sensible | 2 | 3 |
| *Staphylococcus aureus* UC 1 128 Pen-Resistant | 5 | 5 |
| *Staphylococcus aureus* exp. n° 54 146 | 3 | 5 |
| *Streptococcus pyogenes* A 561 | 0,1 | 0,1 |
| *Streptococcus faecalis* 5 432 | 5 | 20 |
| *Streptococcus faecalis* 99 F 74 | 20 | >40 |
| *Bacillus subtilis* ATCC 6 633 | 0,5 | 1 |
| *Escherichia Coli* Sensible Tetracycline ATCC 9 637 | 0,2 | 0,5 |
| *Escherichia Coli* Resistant Tetracycline ATCC 11 303 | 0,05 | 0,05 |
| *Escherichia Coli* Exp. $TO_{26}B_6$ | 0,1 | 0,1 |
| *Escherichia Coli* Resistant Gentamicine, Tobramycine R 55 123 D | 0,1 | 0,1 |
| *Klebsiella pneumoniae* Exp. 52 145 | 0,05 | 0,05 |
| *Klebsiella pneumoniae* 2 536 Resistant Gentamycine | 0,5 | 0,5 |
| *Proteus mirabilis* (indol −) A 235 | 0,1 | 0,1 |
| *Proteus vulgaris* (indol +) A 232 | 5 | 40 |
| *Salmonella typhimurium* 420 | 0,2 | 0,2 |
| *Enterobacter cloacae* 681 | 2 | 10 |
| *Providencia Du* 48 | 5 | 5 |
| *Serratia* Resistant Gentamicine 2 532 | 2 | 2 |

PRODUCT OF EXAMPLE 14

| STRAIN | MIC in μg/ml | |
|---|---|---|
| | 24 H | 48 H |
| *Staphylococcus aureus* ATCC 6 538 Pen-Sensible | 20 | 20 |
| *Staphylococcus aureus* UC 1 128 Pen-Resistant | 20 | 40 |
| *Staphylococcus aureus* exp. n° 54 146 | 20 | >40 |
| *Streptococcus pyogenes* A 561 | 1 | 1 |
| *Streptococcus faecalis* 5 432 | >40 | >40 |
| *Streptococcus faecalis* 99 F 74 | >40 | >40 |
| *Bacillus subtilis* ATCC 6 633 | 10 | >40 |
| *Escherichia Coli* Sensible Tetracycline ATCC 9 637 | 0,5 | 0,5 |
| *Escherichia Coli* Resistant Tetracycline ATCC 11 303 | 0,2 | 0,2 |
| *Escherichia Coli* Exp. $TO_{26}B_6$ | 0,5 | 0,5 |
| *Escherichia Coli* Resistant Gentamicine, Tobramycine R 55 123 D | 0,5 | 0,5 |
| *Klebsiella pneumoniae* Exp. 52 145 | 1 | 1 |
| *Klebsiella pneumoniae* 2 536 Resistant Gentamycine | 1 | 1 |
| *Proteus mirabilis* (indol −) A 235 | 0,05 | 0,05 |
| *Proteus vulgaris* (indol +) A 232 | 0,1 | 3 |
| *Salmonella typhimurium* 420 | 1 | 1 |
| *Enterobacter cloacae* 681 | 40 | >40 |
| *Providencia Du* 48 | 2 | 3 |
| *Serratia* Resistant Gentamicine 2 532 | 1 | 1 |

Various modifications of the products and processes of the invention may be made without departing from the spirit or scope thereof and it should be understood that the invention is to be limited only as defined in the appended claims.

We claim:

1. Syn isomers of a 7-amino-thiazolyl-acetamido-3-acetoxymethyl-cephalosporanic acid compound of the formula

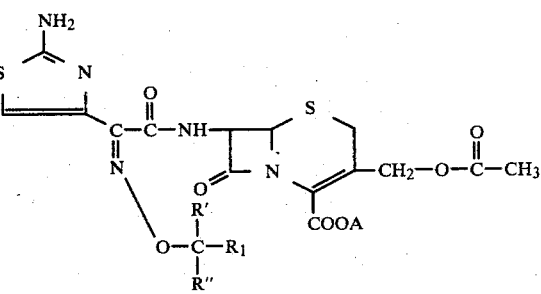

wherein $R_1$ is selected from the group consisting of —CN, —$CONH_2$ and —$COOR_1'$, $R_1'$ is selected from the group consisting of alkyl of 1 to 3 carbon atoms, hydrogen, alkali metal, alkaline earth metal, ammonium and a non-toxic, pharmaceutically acceptable organic amine, A is selected from the group consisting of hydrogen, alkali metal, alkaline earth metal, ammonium and a non-toxic, pharmaceutically acceptable organic amine, and when $R_1'$ is other than alkyl, $R_1'$ and A are the same, R' and R" are individually selected from the group consisting of hydrogen and alkyl of 1 to 3 carbon atoms with the

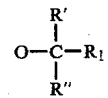

group in the syn position with the proviso that when $R_1$ is —$COOR_1'$ and $R_1'$ is hydrogen, A is hydrogen and when $R_1$ is —$COOR_1'$ and $R_1'$ is an alkali metal, alkaline earth metal, ammonium or a non-toxic, pharmaceutically acceptable organic amine, A has the same meaning as $R_1'$.

2. A compound of claim 1 wherein $R_1$ is —$COOR_1'$ and R' and R" are hydrogen.

3. A compound of claim 1 selected from the group consisting of the syn isomer of 7-[2-(2-amino-4-thiazolyl)-2-(carbethoxymethyloxyimino)-acetamido]-3-acetoxymethyl-ceph-3-eme-4-carboxylic acid and its salts with alkali metal, alkaline earth metal, ammonium and an non-toxic, pharmaceutically acceptable organic amine.

4. A compound of claim 1 selected from the group consisting of the syn isomer of 7-[2-(2-amino-4-thiazolyl)-2-(hydroxycarbonylmethoxyimino)-acetamido]-3-acetoxymethylceph-3-eme-4-carboxylic acid and its salts with alkali metal, alkaline earth metal, ammonium and a non-toxic, pharmaceutically acceptable organic amine.

5. A compound of claim 1 selected from the group consisting of the syn isomer of 7-[2-(2-amino-4-thiazolyl)-2-(cyanomethyloxyimino)-acetamido]-3-acetoxymethyl-ceph-3-eme-4-carboxylic acid and its salts with alkali metal, alkaline earth metal, ammonium and a non-toxic, pharmaceutically acceptable organic amine.

6. A compound of claim 1 selected from the group consisting of the syn isomer of 7-[2-(2-amino-4-thiazolyl-2-(aminocarbonylmethyloxyimino)-acetamido]-3-acetoxymethyl-ceph-3-eme-4-carboxylic acid and its salts with alkali metal alkaline earth metal, ammonium and a non-toxic, pharmaceutically acceptable organic amine.

7. A compound of claim 1 selected from the group consisting of the syn isomer of 7-[2-(2-amino-4-thiazolyl)-2-(1-carboxy-1-methylethyloxyimino)-acetamido]-3-acetoxymethyl-ceph-3-eme-4-carboxylic acid and its salts with alkali metal, alkaline earth metal, ammonium and a non-toxic, pharmaceutically acceptable organic amine.

8. A compound of claim 1 which is the syn isomer of disodium 7-[2-(2-amino-4-thiazolyl)-2-(hydroxycarbonylmethloxyimino)-acetamido]-3-acetoxymethyl-ceph-3-eme-4-carboxylate.

9. A compound of claim 1 which is the syn isomer of sodium 7-[2-(2-amino-4-thiazolyl)-2-(cyanomethyloxyimino)-acetamido]-3-acetoxymethyl-ceph-3-eme-4-carboxylate.

10. A compound of claim 1 which is the syn isomer of sodium 7-[2-(2-amino-4-thiazolyl)-2-(aminocarbonylmethyloxyimino)-acetamido]-3-acetoxymethyl-ceph-3-eme-4-carboxylate.

11. A compound of claim 1 which is the syn isomer of disodium 7-[2-(2-amino-4-thiazolyl)-2-(1-carboxy-1-methylethyloxyimino)-acetamido]-3-acetoxymethyl-ceph-3-eme-4-carboxylate.

12. An antibacterial composition comprising an antibacterially effective amount of at least one compound of claim 1 and an inert pharmaceutical carrier.

13. A composition of claim 12 wherein $R_1$ is —COOR$_1'$ and R' and R" are hydrogen.

14. A method of combatting bacterial infections in warm-blooded animals comprising administering to warm-blooded animals an antibacterially effective amount of at least one compound of claim 1.

15. A method of claim 14 wherein $R_1$ is —COOR$_1'$ and R' and R" are hydrogen.

16. A method of claim 14 selected from the group consisting of the syn isomer of 7-[2-(2-amino-4-thiazolyl)-2-(carbethoxymethoxyimino)-acetamido]-3-acetoxymethyl-ceph-3-eme-4-carboxylic acid and its salts with alkali metal, alkaline earth metal, ammonium and a non-toxic, pharmaceutically acceptable organic amine.

17. A method of claim 14 selected from the group consisting of the syn isomer of 7-[2-(2-amino-4-thiazolyl)-2-(hydroxycarbonylmethyloxyimino)-acetamido]-3-acetoxymethyl-ceph-3-eme-4-carboxylic acid and its salts with alkali metal, alkaline earth metal, ammonium and a non-toxic, pharmaceutically acceptable organic amine.

18. A method of claim 14 selected from the group consisting of the syn isomer of 7-[2-(2-amino-4-thiazolyl)-2-(cyanomethyloxyimino)-acetamido]-3-acetoxymethyl-ceph-3-eme-4-carboxylic acid and its salts with alkali metal, alkaline earth metal, ammonium and a non-toxic, pharmaceutically acceptable organic amine.

19. A method of claim 14 selected from the group consisting of the syn isomer of 7-[2-(2-amino-4-thiazolyl)-2-(aminocarbonylmethyloxyimino)-acetamido]-3-acetoxymethyl-ceph-3-eme-4-carboxylic acid and its salts with alkali metal, alkaline earth metal, ammonium and a non-toxic, pharmaceutically acceptable organic amine.

20. A method of claim 14 selected from the group consisting of the syn isomer of 7-[2-(2-amino-4-thiazolyl)-2-1-carboxy-1-methylethyloxyimino)-acetamido-]-3-acetoxymethyl-ceph-3-eme-4-carboxylic acid and its salts with alkali metal, alkaline earth metal, ammonium and a non-toxic, pharmaceutically acceptable organic amine.

21. A method of claim 14 which is the syn isomer of disodium 7-[2-(2-amino-4-thiazolyl)-2-(hydroxycarbonylmethyloxyimino)-acetamido]-3-acetoxymethyl-ceph-3-eme-4-carboxylate.

22. A method of claim 14 which is the syn isomer of sodium 7-[2-(2-amino-4-thiazolyl)-2-(cyanomethyloxyimino)-acetamido]-3-acetoxymethyl-ceph-3-eme-4-carboxylate.

23. A method of claim 14 which is the syn isomer of sodium 7-[2-(2-amino-4-thiazolyl)-2-(aminocarbonylmethyloxyimino)-acetamido]-3-acetoxymethyl-ceph-3-eme-4-carboxylate.

24. A method of claim 14 which is the syn isomer of disodium 7-[2-(2-amino-4-thiazolyl)-2-(1-carboxy-1-methylethoxyimino)-acetamido]-3-acetoxymethyl-ceph-3-eme-4-carboxylate.

* * * * *

UNITED STATES PATENT AND TRADEMARK OFFICE
CERTIFICATE OF CORRECTION

PATENT NO. : 4,288,434  Page 1 of 4
DATED : September 8, 1981
INVENTOR(S) : Rene Heymes It is certified that error appears in the above—identified patent and that said Letters Patent is hereby corrected as shown below:

Column 2, line 10: "carbethox-" should read -- carbethoxy- --.

Column 2, line 11: "ymethyloxyimino" should read -- methyloxyimino --.

Column 2, line 33; Column 20, line 6: "aminocarbonylmethylox-" should read -- aminocarbonylmethyloxy- --.

Column 2, line 34; column 18, line 32; column 20, lines 7, 23, 45; column 21, lines 26, 31; column 22, lines 8, 47; column 23, lines 12, 24; column 25, line 38; column 27, lines 45, 58; column 32, lines 23, 38:
"yimino" should read -- imino --.

Column 5, line 32: "alcoholwater" should read -- alcohol-water --.

Column 12, line 59, column 13, lines 52 and 68: "carbethoxymethylox-" should read -- carbethoxymethyloxy- --.

Column 14, line 1: "yiminoacetamido" should read -- imino-acetamido --.

Column 14, line 36; Column 18, line 16: "brom-" should read -- bromo- --.

Column 14, line 37; Column 18, line 17: "oacetate" should read -- acetate --.

Column 15, lines 24-25: "hydrochlo-ride acid" should read -- hydrochlo-ric acid --.

UNITED STATES PATENT AND TRADEMARK OFFICE
CERTIFICATE OF CORRECTION

PATENT NO. : 4,288,434

DATED : September 8, 1981

INVENTOR(S) : Rene Heymes

It is certified that error appears in the above—identified patent and that said Letters Patent is hereby corrected as shown below:

Column 15, line 40: "methylceph" should read -- methyl-ceph --.

Column 15, line 46; column 16, line 12: "hydroxycarbonylmethox-" should read -- hydroxycarbonylmethoxy- --.

Column 16, line 7; Column 18, lines 33, 65; Column 19, line 18: "CH-" should read -- $CH_2$- --.

Column 16, line 8; Column 18, lines 34, 66; Column 19, line 19: Delete "$_2$-"

Column 16, line 34: "cyanomethylox-" should read -- cyanomethyloxy- --.

Column 18, line 31: "ethylcarboxymethylox-" should read -- ethylcarboxymethyloxy- --.

Column 19, second last line; Column 20, line 41; Column 22, line 1; Column 25, line 49; Column 26, line 14; Column 27, line 65:
"acetox-" should read -- acetoxy- --.

Column 19, last line; Column 20, line 42; Column 22, line 2; Column 25, line 50; Column 26, line 15; Column 27, line 66:
"ymethyl" should read -- methyl --.

Column 20, line 22: "aminocarbonylmethox-" should read -- aminocarbonylmethoxy- --.

Column 20, line 44; Column 21, lines 25, 30: "methylethylox-" should read -- methylethyloxy- --.

UNITED STATES PATENT AND TRADEMARK OFFICE
CERTIFICATE OF CORRECTION

PATENT NO. : 4,288,434

DATED : September 8, 1981

Page 3 of 4

INVENTOR(S) : Rene Heymes

It is certified that error appears in the above—identified patent and that said Letters Patent is hereby corrected as shown below:

Column 21, line 42: "either" should read -- ether --

Column 22, line 7: "methylethox-" should read -- methylethoxy- --.

Column 22, line 46; Column 23, lines 11, 23; Column 25, line 37: "methoxyethox-" should read -- methoxyethoxy- --.

Column 27, line 15: "butox-" should read -- butoxy- --.

Column 27, lines 16, 55: "ycarbonylmethyloxyimino" should read -- carbonylmethyloxyimino --.

Column 27, line 20: "(CDCl$_3$ 13 60 MHz)" should read -- (CDCl$_3$ - 60 MHz) --.

Column 27, line 44: "carboxymethylox-" should read -- carboxymethyloxy- --.

Column 27, line 54: "hydrox-" should read -- hydroxy- --.

Column 27, line 57; Column 31, line 22 (claim 9); Column 32, line 37 (claim 22): "cyanomethylox-   " should read --cyanomethyloxy- --.

Column 29, line 8: "Esherichia" should read -- Escherichia --.

Column 31, line 46 (claim 16): "carbethoxymethoxyimino" should read -- carbethoxymethyloxyimino --.

UNITED STATES PATENT AND TRADEMARK OFFICE
CERTIFICATE OF CORRECTION

PATENT NO. : 4,288,434

DATED : September 8, 1981

INVENTOR(S) : Rene Heymes

It is certified that error appears in the above—identified patent and that said Letters Patent is hereby corrected as shown below:

Column 32, line 46 (claim 24): "methylethoxyimino" should read -- methylethyloxyimino --.

Signed and Sealed this

Sixth Day of April 1982

[SEAL]

Attest:

Attesting Officer

GERALD J. MOSSINGHOFF

Commissioner of Patents and Trademarks